(12) United States Patent
Zhou et al.

(10) Patent No.: US 9,102,691 B2
(45) Date of Patent: Aug. 11, 2015

(54) ALUMINUM METAL ORGANIC FRAMEWORK MATERIALS

(71) Applicant: TEXAS A&M UNIVERSITY SYSTEM, College Station, TX (US)

(72) Inventors: Hong-Cai Zhou, College Station, TX (US); Dawei Feng, College Station, TX (US); Kecheng Wang, College Station, TX (US)

(73) Assignee: Texas A&M University System, College Station, TX (US)

( * ) Notice: Subject to any disclaimer, the term of this patent is extended or adjusted under 35 U.S.C. 154(b) by 0 days.

(21) Appl. No.: 14/555,535

(22) Filed: Nov. 26, 2014

(65) Prior Publication Data

US 2015/0152123 A1    Jun. 4, 2015

Related U.S. Application Data

(60) Provisional application No. 61/909,149, filed on Nov. 26, 2013.

(30) Foreign Application Priority Data

| Aug. 8, 2014 | (GB) | 1414113.9 |
| Aug. 8, 2014 | (GB) | 1414114.7 |
| Aug. 8, 2014 | (GB) | 1414115.4 |
| Aug. 8, 2014 | (GB) | 1414117.0 |

(51) Int. Cl.

| *B01D 53/02* | (2006.01) |
| *B01J 20/22* | (2006.01) |
| *C07F 5/06* | (2006.01) |
| *B01J 20/28* | (2006.01) |
| *C01B 3/50* | (2006.01) |
| *C01B 3/00* | (2006.01) |
| *C01B 31/20* | (2006.01) |
| *C01B 21/04* | (2006.01) |
| *C07C 7/13* | (2006.01) |

(52) U.S. Cl.
CPC .............. *C07F 5/069* (2013.01); *B01J 20/226* (2013.01); *B01J 20/28057* (2013.01); *B01J 20/28069* (2013.01); *C01B 3/0015* (2013.01); *C01B 3/508* (2013.01); *C01B 21/0455* (2013.01); *C01B 31/20* (2013.01); *C07C 7/13* (2013.01); *C01B 2210/0015* (2013.01)

(58) Field of Classification Search
CPC ........ B01J 20/22; B01J 20/226; B01D 53/02; B01D 2253/204; B01D 2253/304; B01D 2253/308; B01D 2253/311; B01D 2257/102; B01D 2257/108; B01D 2257/504; B01D 2257/7025; B01D 2253/306
USPC ........ 96/108; 95/90, 116, 130, 139, 143, 902; 502/401, 439, 526
See application file for complete search history.

(56) References Cited

U.S. PATENT DOCUMENTS

| 8,337,591 | B2 * | 12/2012 | Zhou et al. | 95/90 |
| 8,648,002 | B2 * | 2/2014 | Schubert et al. | 502/150 |
| 2009/0092818 | A1 * | 4/2009 | Kiener et al. | 428/304.4 |
| 2010/0154635 | A1 * | 6/2010 | Schubert et al. | 95/90 |
| 2011/0319604 | A1 * | 12/2011 | Loiseau et al. | 534/602 |
| 2012/0055880 | A1 * | 3/2012 | Loiseau et al. | 210/660 |
| 2012/1677761 | * | 7/2012 | Kiener et al. | 95/96 |
| 2013/0129608 | A1 * | 5/2013 | Watanabe et al. | 423/648.1 |
| 2014/0212944 | A1 * | 7/2014 | Tian et al. | 435/180 |
| 2015/0047505 | A1 * | 2/2015 | Schroder et al. | 95/129 |

OTHER PUBLICATIONS

Vokringer et al. "Synthesis, Single-Crystal X-ray Microdiffraction, and NMR Characterizations of the Giant Pore Metal-Organic Framework Aluminum Trimesate MIL-100" (2009) Chem. Mater. 21, 5695-5697.*

Volkringer et al. "Occurrence of Uncommon Infinte Chains Consisting of Edge-Sharing Octahedra in a Porous Metal Organic Framework-Type Aluminaum Pyromellitate AI4(OH)8[C10O8H2] (MIL-120): Synthesis, Structure, and Gas Sorption Properties" (2009) Chem. Mater. 21, 5783-5791.*

* cited by examiner

*Primary Examiner* — Frank Lawrence
(74) *Attorney, Agent, or Firm* — Reising Ethington P.C.

(57) ABSTRACT

The invention relates to monocrystalline single crystals of metal-organic framework materials comprising at least one aluminum metal ion, processes for preparing the same, methods for employing the same, and the use thereof. The invention also relates to monocrystalline aluminum metal-organic frameworks.

18 Claims, 6 Drawing Sheets

ALUMINUM METAL ORGANIC FRAMEWORK MATERIALS

STATEMENT REGARDING FEDERALLY SPONSORED RESEARCH OR DEVELOPMENT

This invention was made with government support under DE-AR0000073 awarded by the U.S. Dept. of Energy. The government has certain rights in the invention.

FIELD OF THE INVENTION

The present invention relates to aluminium metal-organic frameworks, processes for preparing the same and the use thereof as well as aluminium metal-organic frameworks in crystalline form. In particular, the invention relates to polycrystalline and monocrystalline aluminium metal organic frameworks and to a method for preparing the same. More specifically, it relates to massive single crystal aluminium metal organic frameworks and to their methods of preparation.

BACKGROUND OF THE INVENTION

Metal-Organic Frameworks (MOFs) have garnered significant interests in the last two decades due to their promising potential in many applications such as gas adsorption, separation, catalysis and sensing. For example, see Yaghi, O. M.; O'Keeffe, M.; Ockwig, N. W.; Chae, H. K.; Eddaoudi, M.; Kim, J. Nature 2003, 423, 705. (b) Ferey, G.; Mellot-Draznieks, C.; Serre, C.; Millange, F. Acc. Chem. Res. 2005, 38, 217. (c) Horike, S.; Shimomura, S.; Kitagawa, S. Nat. Chem. 2009, 1, 695. (d) Seo, J. S.; Whang, D.; Lee, H.; Jun, S. I.; Oh, J.; Jeon, Y. J.; Kim, K. Nature 2000, 404, 982. (e) Jiang, H.-L.; Liu, B.; Akita, T.; Haruta, M; Sakurai, H.; Xu, Q. J. Am. Chem. Soc. 2009, 131, 11302. (f) Kreno, L. E.; Leong, K.; Farha, 0. K.; Allendorf, M.; Van Duyne, R. P.; Hupp, J. T. Chem. Rev. 2012, 112, 1105. (g) Yang, S.; Liu, L.; Sun, J.; Thomas, K. M.; Davies, A. J.; George, M. W.; Blake, A. J.; Hill, A. H.; Fitch, A. N.; Tang, C. C.; Schröder, M. J. Am. Chem. Soc. 2013, 135, 4954. (h) Bloch, E. D.; Queen, W. L.; Krishna, R.; Zadrozny, J. M.; Brown, C. M.; Long, J. R. Science 2012, 335, 1606. (i) Wang, Z.; Cohen, S. M. Chem. Soc. Rev. 2009, 38, 1315.

Compared with other porous materials such as zeolite and mesoporous silica, MOFs are based on crystalline porous structures tunable on the atomic scale, which can be designed and functionalized by judicious choice of metal nodes and modification of the organic linkers. However, one of the limitations of most MOFs is their low chemical stability, which undoubtedly hampers their application in industry. A rule of thumb for the construction of stable MOFs comes from the simple Hard and Soft Acid and Base Theory, which guides the selection of the metal-ligand combination for a MOF. For example, see Pearson, R. G. J. Am. Chem. Soc. 1963, 85, 3533. Because the carboxylate group is a hard Lewis base, hard Lewis acids such as $Fe^{3+}$, $Cr^{3+}$, $Zr^{4+}$ and $Ti^{4+}$ are usually considered good candidates for the construction of robust MOFs. This method has become the focus of some recent research efforts but very few stable MOFs have been obtained, especially in single crystal form. For example, see (a) Cavka, J. H.; Jakobsen, S.; Olsbye, U.; Guillou, N.; Lamberti, C.; Bordiga, S.; Lillerud, K. P. J. Am. Chem. Soc. 2008, 130, 13850. (b) Ferey, G.; Serre, C. Chem. Soc. Rev. 2009, 38, 1380. (c) Phan, A.; Doonan, C. J.; Uribe-Romo, F. J.; Knobler, C. B.; O'Keeffe, M.; Yaghi, O. M. Acc. Chem. Res. 2010, 43, 58. (d). Murray, L. J.; Dincă, M.; Yano, J.; Chavan, S.; Bordiga, S.; Brown, C. M.; Long. J. R. J. Am. Chem. Soc. 2010, 132, 7856. (e) Feng, D.; Gu, Z.-Y.; Li, J.-R.; Jiang, H.-L.; Wei, Z.; Zhou, H.-C. Angew. Chem. Int. Ed. 2012, 51, 10307. (f) Jiang, H.-L.; Feng, D.; Liu, T.-F.; Li, J.-R.; Zhou, H.-C. J. Am. Chem. Soc. 2012, 134, 14690. The main reason is that MOFs based on these metal ions of high valence are difficult to crystallize. Occasionally, MOFs in the form of crystalline powder were obtained, but structure solution and refinement based on Powder X-Ray Diffraction (PXRD) data is not straightforward. Furthermore, the incorporation of rarely reported metal nodes into MOFs is less predictable and controllable.

Metal-organic frameworks have many applications including, for example, in the field of adsorption, storage, separation or controlled release of chemical substances, such as, for example gases, or in the field of catalysis. Metal-organic frameworks may also be useful in the field of pharmaceuticals (controlled release of medicaments) and in the field of cosmetics.

There are in fact a growing number of applications for metal-organic frameworks and as such there is an ever growing need for new such materials with a variety of properties and a need for new metal-organic frameworks having improved properties.

In addition, there is a need to develop new processes for preparing metal-organic frameworks that allow for the preparation of a wide variety of metal-organic frameworks and/or improve the quality of the metal-organic frameworks obtained.

However, metal organic (framework) powder material has been prepared by various methods but prior to the present invention large single crystals of metal organic frameworks containing a number of different metal ions have not been prepared. In particular, monocrystalline and polycrystalline aluminium metal organic frameworks have not been prepared prior to the present invention. In fact, serious difficulties have been experienced preparing crystalline metal organic frameworks containing aluminium.

For aluminium MOFs, reports of successful preparations of aluminium MOFs are rare. In the literature, Ferey et al (Chem. Mater. 2009, 21, 5695-5697 & Chem. Mater. 2009, 21, 5783-5791) describe the preparation of aluminium MOFs (labelled as MIL-100, MIL-120, and MIL-121) using hydrothermal synthesis, which were also the subject of US patent application US2012/0055880 A1. The sizes of the crystals obtained were however relatively small. For example, US2012/0055880 reports crystal sizes ranging from 1 micron up to only 30 microns (0.001 mm to 0.03 mm). Ferey et al therefore fail to provide aluminium MOFs having a large crystal size.

In addition, U.S. Pat. No. 8,648,002 describes the preparation of an aluminium MOF. However, this MOF (MOF-53) is in fact amorphous and as a result exhibits very small particle size in the region of 350 manometers. U.S. Pat. No. 8,648,002 therefore fails to prepare an aluminium MOF which is crystalline, let alone which is polycrystalline or monocrystalline and having large crystal sizes.

All these references highlight that despite a significant effort to prepare aluminium MOFs exhibiting large crystal sizes and monocrystalline characteristics, all such attempts have failed. There are therefore clearly great difficulties associated with the preparation of aluminium metal organic framework materials having the desired properties.

In the case of aluminium MOFs, there is therefore a need to provide crystalline MOFs that exhibit a greater crystal size and a minimum degree of crystallinity. As well as providing crystalline products, there is also a need to provide MOFs in monocrystalline and polycrystalline form. A monocrystalline MOF (or a single crystal MOF) consists of a MOF in which the crystal lattice of the entire solid is continuous, unbroken (with no grain boundaries) to its edges. Monocrystalline is opposed to amorphous material, in which the atomic order is limited to short range order only. Polycrystalline materials lie between these two extremes; they are made up of small crystals. They are different from amorphous materials. Large single crystals are very rare in nature and can be difficult to produce in the laboratory.

Metal-organic frameworks are coordination polymers having an inorganic-organic hybrid framework that comprises metal ions and organic ligands coordinated to the metal ions. These materials are three-dimensional, e.g. they have three-dimensional lattices in which the metallic species are joined together periodically by spacer ligands.

An object of the invention, therefore, is to provide an aluminium based metal organic framework having a large crystal size. Another object is to provide a method of preparing monocrystalline and polycrystalline aluminium metal organic frameworks having a larger crystal size than previously achieved.

SUMMARY OF THE INVENTION

According to a first aspect of the invention is provided a metal-organic framework comprising one or more metal-ligand clusters, each metal-ligand cluster comprising (i) a metal cluster having two or more metal ions, wherein at least one metal ion is aluminium, and (ii) one or more ligands having two or more carboxylate groups.

In one embodiment, the metal organic framework is a single crystal of an aluminium metal organic framework. For example, the crystal may have a size greater than or equal to 2 μm, 5 μm, 10 μm, 20 μm, 30 μm, 40 μm, 50 μm, 100 μm, 150 μm, 200 μm, 300 μm, 500 μm, 750 μm, or 1000 μm. The invention therefore provides aluminium MOFs having crystal sizes that far exceed anything that has been achieved before.

The crystal may have a crystal size ranging from about 25 μm to about 500 μm, preferably from about 50 μm to about 200 μm.

In one embodiment, the metal-organic framework is monocrystalline or polycrystalline.

The aluminium metal organic framework may be functionalised or not functionalised.

In one embodiment, the aluminium metal-organic framework does not comprise an amine functional group.

In one embodiment, the metal-organic framework comprises at least one metal-ligand cluster, each metal-ligand cluster comprising at least one aluminium metal ion. For example, the at least one metal-ligand cluster comprises at least two aluminium metal ions, or the at least one metal-ligand cluster comprises three aluminium metal ions.

In one embodiment, the metal cluster may have a formula $Al_3O$.

In one embodiment, the metal organic framework may have an $Al_3O$ cornerstone.

In one embodiment, the aluminium metal organic framework comprises metal clusters coordinated with 4, 5, or 6 ligands.

In one embodiment, the aluminium metal-organic framework comprises inorganic cornerstones having at least 10 coordination sites, preferably having 12 coordination sites.

In one embodiment, the aluminium metal-organic framework has a molar ratio of metal ions to organic linker of from about 1:0.45 to about 1:0.55, preferably about 1:0.5.

In one embodiment, the aluminium metal-organic framework has a surface area of at least 1000 $m^2/g$, preferably at least 1100 $m^2/g$, more preferably greater than or equal to 1200 $m^2/g$. Likewise, the metal-organic framework may have a surface area of less than or equal to 6000 $m^2/g$, preferably less than or equal to 4000 $m^2/g$, more preferably less than or equal to 3000 $m^2/g$.

In one embodiment, the aluminium metal-organic framework comprises cavities having a free diameter of about 4 Å to about 50 Å, or about 8 Å to about 12 Å, or about 10 Å.

In one embodiment, the aluminium metal-organic framework comprises pores having a pore volume from about 0.1 $cm^3/g$ to about 4 $cm^3/g$, or from about 0.3 $cm^3/g$ to about 0.7 $cm^3/g$, or from about 0.4 $cm^3/g$ to about 0.6 $cm^3/g$, or about 0.5 $cm^3/g$.

In one embodiment, the invention provides a single crystal of a metal-organic framework comprising at least one aluminium metal ion having a largest dimension, for example as observed under a microscope, of greater than or equal to about 2 μM, greater than or equal to 5 μm, 10 μm, 20 μm, 30 μm, 40 μm, 50 μm, 100 μm, or 150 μm. Generally, single crystals of a metal-organic framework comprising at least one aluminium metal ion (e.g. comprising a metal cluster having formula $Al_3O$) having a largest dimension of between about 50 μm and 200 μm have been achieved.

In one embodiment, the present invention provides a single crystal of a metal-organic framework comprising at least one metal-ligand cluster, each metal-ligand cluster comprising at least one aluminium metal ion, preferably at least two aluminium metal ions, more preferably three aluminium metal ions, wherein the single crystal has a size greater than or equal to about 2 μm, greater than or equal to 5 μm, 10 μm, 30 μm, 40 μm, 50 μm, 100 μm, or 150 μm. Generally, single crystals of a metal-organic framework comprising at least one aluminium metal ion (e.g. comprising a metal cluster having formula $Al_3O$) having a largest dimension of between about 50 μm and 200 μm have been achieved.

In one embodiment, the invention provides a single crystal of a metal-organic framework comprising at least one aluminium metal ion (e.g. comprising a metal cluster having formula $Al_3O$) having a largest dimension, for example as observed under a microscope, of greater than or equal to about 2 μm, greater than or equal to 5 μm, 10 μm, 20 μm, 30 μm, 40 μm, 50 μm, 100 μm, or 150 μm. Generally, single crystals of a metal-organic framework comprising at least one aluminium metal ion (e.g. comprising a metal cluster having formula $Al_3O$) having a largest dimension of between about 50 μm and 200 μm have been achieved.

In preferred embodiments, the size of the single crystal (containing an aluminium metal ion or an iron metal ion) is greater than or equal to about 5 μm, more preferably greater or equal to than about 10 μm, greater than or equal to about 20 μm, greater than or equal to about 30 μm, greater than or equal to about 40 μm, greater than or equal to about 50 μm.

Aluminium metal-organic frameworks (Al-MOFs) have aroused great interest for a number of reasons such as aluminium is a very cheap and rich element in our planet; aluminium's atomic mass is very light (at least compared to other metal elements, especially the transition metals) which means for the MOFs with iso-structure, Al-MOFs have lower weight and therefore higher specific area, which provides improved gas adsorption; there is a very strong interaction between $Al^{3+}$ and carboxylate groups; and Al-MOFs can exhibit very high moisture, mechanical and chemical stability.

However, a great deal of effort has been put into preparing crystals of Al-MOFs without success. In fact, the inventors are not aware of any one preparing a single crystal of an Al-MOF with a single crystal size greater than about 1 µm.

In one embodiment, the one or more ligands are derived from a dicarboxylic acid, a tricarboxylic acid, a tetracarboxylic acid, a hexacarboxylic acid, or a octacarboxylic acid.

Suitable ligands are described in more detail in the section titled "General".

According to one aspect of the invention is provided a monocrystalline or polycrystalline metal-organic framework comprising at least one aluminium metal ion.

According to one aspect of the invention is provided a monocrystalline or polycrystalline metal-organic framework comprising an $Al_3O$ cornerstone.

In embodiments in which it is necessary to balance the charge of the metal-ligand cluster, additional substituents/ligands may be included. For example, additional hydroxyl groups may be present in the metal-ligand cluster.

The metal-organic frameworks of the invention exhibit high gravimetric and volumetric $H_2$ and $CH_4$ uptake. Additionally, these metal-organic frameworks exhibit extraordinary stability in water and aqueous solutions at a range of pHs.

The metal-organic framework according to the invention may be in crystalline form. Specifically, the present invention may provide a single crystal of a metal-organic framework according to the invention having a largest dimension, for example as measured/observed under a microscope, of greater than or equal to 2 µm, greater than or equal to 5 µm, 10 µm, 20 µm, 30 µm, 40 µm, 50 µm, 100 µm, 200 µm, 500 µm, 1000 µm, or 1500 µm. Generally, single crystals of a metal-organic framework according to the invention possess a largest dimension of between about 50 µm and 2000 µm.

In one embodiment, the invention provides a single crystal of a metal-organic framework comprising at least one aluminium metal ion (e.g. comprising a metal cluster having formula $Al_3O$) having a largest dimension, for example as observed under a microscope, of greater than or equal to about 2 µm, greater than or equal to 5 µm, 10 µm, 20 µm, 30 µm, 40 µm, 50 µm, 100 µm, or 150 µm. Generally, single crystals of a metal-organic framework comprising at least one aluminium metal ion (e.g. comprising a metal cluster having formula $Al_3O$) having a largest dimension of between about 50 µm and 200 µm have been achieved.

In one embodiment, the present invention provides a single crystal of a metal-organic framework comprising at least one metal-ligand cluster, each metal-ligand cluster comprising at least one aluminium metal ion, preferably at least two aluminium metal ions, more preferably three aluminium metal ions, wherein the single crystal has a size greater than or equal to about 2 µm, greater than or equal to 5 µm, 10 µm, 20 µm, 30 µm, 40 µm, 50 µm, 100 µm, or 150 µm. Generally, single crystals of a metal-organic framework comprising at least one aluminium metal ion (e.g. comprising a metal cluster having formula $Al_3O$) having a largest dimension of between about 50 µm and 200 µm have been achieved.

In preferred embodiments, the size of the single crystal (containing an aluminium metal ion) is greater than or equal to about 5 µm, more preferably greater or equal to than about 10 µm, greater than or equal to about 20 µm, greater than or equal to about 30 µm, greater than or equal to about 40 µm, greater than or equal to about 50 µm.

In some embodiments, the metal-organic framework further comprises one or more ligands having two or more carboxylate groups. For example, the metal-organic framework may comprise 4, 5 or 6 of such ligands. These ligands may be derived from diacarboxylic acids, tricarboxylic acids, tetracarboxylic acids, hexacarboxylic acids, or octacarboxylic acids as defined above.

Aluminium metal-organic frameworks (Al-MOFs) have aroused great interest for a number of reasons such as aluminium is a very cheap and rich element in our planet; aluminium's atomic mass is very light (at least compared to other metal elements, especially the transition metals) which means for the MOFs with iso-structure, Al-MOFs have lower weight and therefore higher specific area, which provides improved gas adsorption; there is a very strong interaction between $Al^{3+}$ and carboxylate groups; and Al-MOFs can exhibit very high moisture, mechanical and chemical stability.

However, a great deal of effort has been put into preparing crystals of Al-MOFs without success. In fact, the inventors are not aware of any one preparing a single crystal of an Al-MOF with a single crystal size greater than about 1 µm. The same is true for iron-MOFs.

According to a further aspect, the invention provides a process for preparing a metal-organic framework as described above, the process comprising reacting a starting compound having formula $M_aO_y(OR_1)_b(R_2COO)_c$ with a ligand precursor having at least two carboxylic acid groups in the presence of an acid having one carboxylic acid or carboxylate group to provide a metal-organic framework comprising a $M_aO$ cluster where at least one $(R_2COO)$ ligand is replaced by at least one ligand having at least two carboxylate groups; wherein each M is independently a metal ion selected from the group consisting of Group 2 through Group 16 metals; $R_1$ is H, alkyl or aryl; $R_2$ is alkyl or aryl; a is an integer from 1 to 8; b is an integer from 0 to 6; c is an integer from 6 to 20; and y is an integer from 1 to 10; wherein at least one M is Al.

Preferably, the acid having one carboxylic acid group or one carboxylate group is selected from trifluoroacetic acid, benzoic acid, formic acid, propionic acid, sodium acetate, and acetic acid. Most preferred is acetic acid.

Preferably, $R_1$ is H.

Preferably, $R_2$ is $CH_3$.

Preferably, a=3.

The starting compound may adopt a number of different combinations of M, a, b, c, and y.

For example, in one embodiment, one or more M=Al, a=3, b=0, c=6, and y=1.

In a preferred embodiment is provided a process for preparing a metal-organic framework comprising a metal ion cluster of formula $M_3O$, the process comprising reacting a starting compound of formula $M_3O(CH_3COO)_6$ with a ligand precursor having at least two carboxylic acid groups in the presence of an acid having one carboxylic acid group or one carboxylate group to provide a metal-organic framework comprising a $M_3O$ cluster where at least one $(CH_3COO)$ ligand is replaced by at least one ligand having at least two carboxylate groups; wherein each M is independently a metal ion selected from the group consisting of Group 2 through Group 16 metals; wherein at least one M is Al.

In some embodiments, the acid having a carboxylic acid group is selected from trifluoroacetic acid, benzoic acid, formic acid, propionic acid, sodium acetate, and acetic acid. Most preferred is acetic acid.

In preferred embodiments, the starting compound has formula $Al_2XO(CH_3COO)_6$, wherein X is a metal ion selected from the group consisting of Group 2 through Group 16 metals. For example, X may be a metal ion selected from Al(III), Fe(II,III), Co(II), Ni(II), Mn(II), Zn(II), Mg(II), Cr(III), V(III), Sc(III), Ca(II), Ba(II) or In(III), preferably X is a metal ion selected from Fe(II,III), Co(II), Ni(II), Mn(II), Zn(II), and Mg(II).

For example, the starting compound may have a formula or $Al_2XO(CH_3COO)_6$, wherein X is Fe(II,III), Al(III), Co(II), Ni(II), Mn(II), Zn(II), or Mg(II). For example, the starting compound may have a formula $Al_3O(CH_3COO)_6$.

In one embodiment, the starting compound has a formula $Al_2XO(CH_3COO)_6$ or $Al_3O(CH_3COO)_6$, wherein X is as defined above. For example, X may be Fe(III), Cr(III), V(III), Sc(III) or In(III).

In one embodiment, the process is a solvothermal process.

In one embodiment, the process involves heating the reaction at elevated pressure.

The inventors have discovered that the use of starting compounds of formula $M_3O(CH_3COO)_6$ in the synthesis of metal-organic frameworks, in particular aluminium containing metal-organic frameworks enable the synthesis of large single crystals of these materials.

The process of the invention may be carried out using any suitable solvent. However, the following solvents are appropriate: acetic acid, water, DMF, DEF, NMP, DMSO and DMA. Acetic acid is preferred.

The amount of acid may vary depending on the ligands involved. However, an appropriate concentration of acid (such as pure glacier acetic acid) is from about 0.001 mmol/l to about 17.4 mol/l. Alternatively, an acid:solvent volume ratio of from about 0.05:2.0 to about 1.2:2.0 may be employed. Preferably, the acid:solvent ratio is from about 0.1:2.0 to about 1:2, from 0.1:2 to about 0.8:2, from about 0.1:2 to about 0.5:2, or an acid:solvent ratio of 0.1:2, 0.15:2, 0.2:2, 0.22:2, 0.25:2, 0.3:2, 0.35:2, 0.4:2, 0.45:2, 0.5:2, 0.6:2, 0.8:2, or 1:2. It is also clear from the examples which of these ratios are preferred for the synthesis of each metal-ligand cluster.

An appropriate acid:solvent ratio is 0.9-1.1:2 (1:2). Preferably, the acid is acetic acid.

Previously, MOFs were synthesized through one pot reactions, in which their inorganic building blocks assemble in situ without adequate control. Therefore, the overall design of MOFs was challenging and significantly limited. As a result, the overall design of MOFs has been dominated by changes to the organic synthesis of these materials. In contrast, the structure of MOFs can be made more predictable using the process of the invention with control of the inorganic building blocks used. Constructed with desired inorganic building blocks, the structure of MOFs becomes more designable and predictable. Meanwhile, stability and functionality can be better controlled for targeted applications, such as gas storage, separations, and catalysis.

In previous MOF one pot reactions, the inorganic building block forms in situ. Without accurate control of the inorganic building blocks, design of MOFs has mainly been dominated by organic synthesis techniques such as ligand extension and functionalization. As a result, several problems existed. For example: (i) the overall design of novel MOFs with expected structures or even simple functionalization of existing MOFs for targeted applications becomes very challenging because of the unpredictable configuration of in situ formed inorganic building blocks; (ii) mixed phases often come out together especially in metals with diverse inorganic building blocks such as $Fe^{3+}$; and (iii) the abundant and interesting inorganic cluster chemistry is almost neglected and mainly acts in a supporting role, which severely limits the potential of inorganic chemistry for MOFs' development. The process of the present invention addresses these problems by employing pre-assembled inorganic building blocks, i.e. having formula $M_3O(CH_3COO)_6$.

All previous synthesis processes are essentially based on the labile coordination bond and have never been generalized. In contrast, the process of the present invention involves building MOFs with preformed inorganic building blocks (PIBBs) through simple substitution reactions. This is possible because: (1) the inorganic building block is isolatable and soluble; (2) the inorganic building block is robust enough that the constructing moieties can be perfectly maintained while it undergoes substitution under solvothermal conditions; and (3) it should have high symmetry to allow the facile formation of infinite frameworks with many ligand types. The present invention employs a preassembled $M_3XO(CH_3COO)_6$ starting compound, such as a $Al_3O(CH_3COO)_6$ starting compound to construct metal-organic frameworks such as Al-MOFs through a simple carboxylate substitution reaction.

In particular, $Al_3O(CH_3COO)_6$ starting compounds exhibit excellent solubility and as a result have been found to be excellent starting materials for the purpose of the present invention. Meanwhile, due to the strong electrostatic interaction between $Al^{3+}$ and $\mu_3$-$O_2$— and the strong coordination bond between $Fe^{3+}$ and carboxylate, such basic carboxylate is inherently robust enough to protect the integrity of the inorganic organic building block under solvothermal conditions. Moreover, the cluster itself exhibits pseudo-$D_{3h}$ symmetry (Al and X are indistinguishable in crystallographic refinement, indicating a disordered X position), which makes it easier to form repeating units.

Metal ions with high valency, in particular metal ions such $Al^{3+}$, as a hard Lewis acidic species, bond strongly to carboxylate, and therefore the ligand dissociation process is slow. This results in a rate of insufficient structural reorganization and defect repair that is insufficient to form a long range ordered crystalline structure. Even using $M_3O(CH_3COO)_6$ type starting materials, direct synthesis of metal-organic frameworks, such as Al-MOFs, still gives rise to gel or amorphous products. In contrast, the process of the present invention uses a ligand substitution process.

Unlike soft Lewis acidic species, $Al^{3+}$ bonds strongly with carboxylate which results in a higher $E_a$ for the ligand dissociation process and thus a much slower reaction rate. Since intermediate species keep constant concentration, and temperature variation simultaneously changes both the forward and the reverse reaction rate, the only way to produce a balanced substitution-dissociation process is to slow down the substitution reaction rate. Without wishing to be bound by theory, this is accomplished in the process of the present invention by maintaining an optimal concentration of ligand or cluster by replacing some portion of the solvent with acetic acid, which bonds competitively to the 5-coordinated intermediate. Because it is actually the carboxylate and not the acid doing the substitution, when the deprotonation process is taken into account, extra acetic acid could simultaneously inhibit the deprotonation of ligand, which further slows down the substitution reaction and aids the crystallization process.

Consequently, with the assistance of acetic acid as a competing reagent, large crystals of metal-organic frameworks may be obtained using the process of the present invention. The process of the present invention is useful in obtaining crystalline (monocrystalline) forms of aluminium-containing MOFs.

In a further aspect, the present invention provides a metal-organic framework obtainable by any process of the invention described herein. In particular, the invention provides a metal-organic framework of the present invention described herein obtainable by any process of the present invention described herein.

The metal-organic frameworks according to the invention have a wide range of applications.

According to one aspect, the invention provides a method comprising uptaking at least one substance by a metal-organic framework of the present invention.

For example, the substance may be hydrogen, methane, carbon dioxide or nitrogen.

According to one aspect, the invention provides a method of storing a gas in a metal-organic framework according to the present invention. Alternatively, the invention provides the use of a metal-organic framework according to any embodiment of the present invention for storing a gas. This may be achieved by binding the gas in a plurality of linker channel sites present in the metal-organic framework, for example using van der Waals forces.

The use/method of storing gases in this way may optimise gas storage density and volumetric gas storage.

For example, the gas may be hydrogen, methane, carbon dioxide or nitrogen.

In the above embodiments of the invention, the metal-organic framework may be configured to store methane or hydrogen, for example for fuelling vehicles.

In a further aspect, the present invention provides the use of any metal-organic framework according to the invention for adsorbing a guest molecule, for example a gas molecule such as hydrogen, methane, carbon dioxide or nitrogen. In this respect, the invention also provides a method of adsorbing a guest molecule, for example a gas molecule such as hydrogen, methane, carbon dioxide or nitrogen, comprising contacting a metal-organic framework of the invention with a guest molecule source.

Accordingly, the invention also provides a metal-organic framework according to any embodiment of the present invention, further comprising one or more than one type of guest molecule.

The guest molecule may be a gas molecule such as hydrogen, methane, carbon dioxide or nitrogen.

In fact, in the context of any of the embodiments described herein, the substance, gas molecule, or gas may be selected from:

(a) $H_2$, $N_2$, Ar, $O_2$, $CO_2$, NO, $NO_2$ or CO; or
(b) an alkane (C1-6), alkene (C2-4), alkyne (C2-6), alcohol (C1-6), arene (C6-8) or a substituted version of any of these;
  wherein the alkane may be selected from $CH_4$, $C_2H_6$, $C_3H_8$, $C_4H_{10}$, $C_5H_{12}$ or $C_6H_{14}$; or a cycloalkane (C3-6) selected from the group consisting of $C_3H_6$, $C_4H_8$, $C_5H_{10}$ and $C_6H_{14}$;
  wherein the alkene may be $C_2H_4$, $C_3H_6$, $C_4H_8$, $C_5H_{10}$ or $C_6H_{12}$;
  wherein the alkyne may be $C_2H_2$;
  wherein the alcohol may be methanol, ethanol, n-propanol, isopropanol, n-butanol or isobutanol; or
  wherein the arene may be a substituted arene (C6-8) such as is nitrobenzene, 1,2-dinitrobenzene, 1,3-dinitrobenzene, 1,4-dinitrobenzene, 1,2,4-trinitrobenzene or 1,3,5-trinitrobenzene.

BRIEF DESCRIPTION OF THE DRAWINGS

The invention will now be described further with reference to the following non-limiting examples and the accompanying Figures.

DETAILED DESCRIPTION OF THE INVENTION

Figure 1:
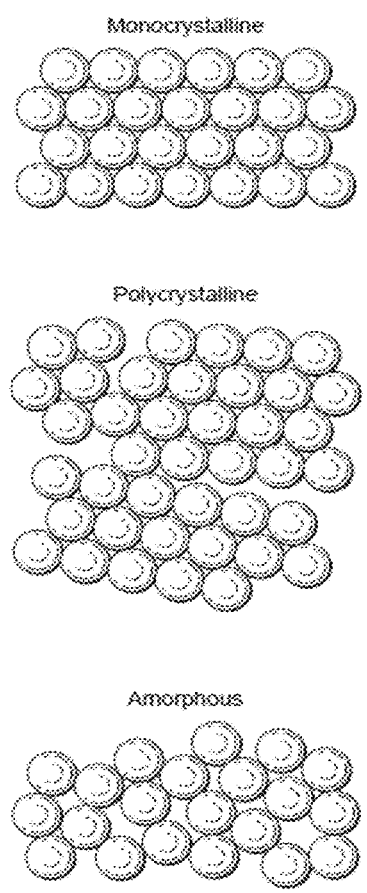
FIG. 1 illustrates the differences between amorphous, polycrystalline, and monocrystalline materials.

A monocrystalline MOF (or a single crystal MOF) consists of a MOF in which the crystal lattice of the entire solid is continuous, unbroken (with no grain boundaries) to its edges. Monocrystalline is opposed to amorphous material, in which the atomic order is limited to short range order only. Polycrystalline materials lie between these two extremes; they are made up of small crystals. A polycrystalline solid or polycrystal is comprised of many individual grains or crystallites. There is no relationship between the grains. Therefore, on a large enough length scale, there is no periodicity across a polycrystalline sample. They are different from monocrystalline materials. Large single crystals are very rare in nature and can be difficult to produce in the laboratory. It is desired that metal organic framework materials should be free from objectionable or incompatible impurities which detrimentally affect the crystal structure or the physical properties of the crystal. The material should be finely divided and uniform in size. Due to the absence of the defects associated with grain boundaries, monocrystalline metal organic frameworks have high surface areas and provide control over the crystallization process. The differences between amorphous, polycrystalline and (mono)crystalline are illustrated in FIG. 1.

The MOF, as achieved by the present invention, is a monocrystalline or polycrystalline product. A single crystal or monocrystalline solid is a material in which the crystal lattice of the entire sample is continuous and unbroken to the edges of the sample, with no grain boundaries. The symmetry exhibited by real single crystals is determined by the crystal structure of the material, normally by single-crystal X-Ray diffraction (SCRD) studies. SCRD is quite accessible in normal chemistry labs and become a routine way to obtain structures of single crystals. In contrast, a polycrystalline solid or polycrystal is comprised of many individual grains or crystallites. In most polycrystalline solids, there is no relationship between neighbouring grains. Therefore, there is no periodicity across a polycrystalline sample. In the absence of single crystals, the structure of polycrystals can be determined by high-resolution powder X-Ray diffraction (PXRD), such as synchrotron resources. However, synchrontron resources are very limited all over the world.

In preferred embodiments of the invention, the metal organic frameworks comprise a low occurrence of twinning. For example, the monocrystalline metal organic frameworks may comprise less than about 5% twinning crystals. Most preferred, the monocrystalline metal organic frameworks comprise no twinning crystals.

In a preferred embodiment, the inorganic cornerstones of the metal organic frameworks of the invention have between 6 and 12 coordination sites. For example, a MOF (preferably monocrystalline) comprising a $Al_3O$ cluster may have 12 coordination sites.

Suitable cornerstones that can be employed in the MOFs of the invention $Al_3O$.

In the context of an aluminium MOF of the present invention, the metal-organic framework may comprise inorganic cornerstones having at least 10 coordination sites, preferably having 12 coordination sites.

In the context of an aluminium MOF of the present invention, the metal-organic framework may have a molar ratio of metal ions to organic linker of from about 1:0.45 to about 1:0.55, preferably about 1:0.5.

In the context of an aluminium MOF of the present invention, the metal-organic framework may have a surface area of at least 1000 $m^2/g$, preferably at least 1100 $m^2/g$, more preferably greater than or equal to 1200 $m^2/g$.

In the context of an aluminium MOF of the present invention, the metal-organic framework may have a surface area of less than or equal to 6000 $m^2/g$, preferably less than or equal to 4000 $m^2/g$, more preferably less than or equal to 3000 $m^2/g$.

In the context of an aluminium MOF of the present invention, the metal-organic framework may comprise cavities having a free diameter of about 8 Å to about 12 Å, preferably about 10 Å.

In the context of an aluminium MOF of the present invention, the metal-organic framework may comprise pores having a pore volume from about 0.3 $cm^3/g$ to about 0.7 $cm^3/g$, preferably about 0.5 $cm^3/g$.

General:

All aspects and embodiments of the invention employ carboxylate ligands. In all aspects and embodiments, these ligands may be derived from a dicarboxylic acid, a tricarboxylic acid, a tetracarboxylic acid, a hexcarboxylic acid or an octacarboxylic acid.

For the purposes of the present invention, the term "derived" means that the carboxylic acid compounds are present in partly deprotonated or fully deprotonated form.

For example, a ligand may be derived from a dicarboxylic acid, such as, for instance, oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptane-canedicarboxylic acid, acetylenedicarboxylic acid, 1,2-benzene-dicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzene-dicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimidedicarboxylic acid, pyridine-2,6-dicarboxylic acid, 2-methylimidazole-4,5-dicarboxylic acid, thiophene-3,4-dicarboxylic acid, 2-isopropylim idazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclo-hexadiene-1,2-dicarboxylic acid, octanedicarboxylic acid, pentane-3,3-dicarboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis(phenylamino)benzene-2,5-dicarboxylic acid, 1,1'-binaphthyidicarboxylic acid, 7-chloro-8-methylquinoline-2,3-dicarboxylic acid, 1-anilinoanthraquinone-2,4'-dicarboxylic acid, poly-tetrahydrofuran-250-dicarboxylic acid, 1,4-bis(carboxymethyl)piperazine-2,3-dicarboxylic acid, 7-chloroquinoline-3,8-dicarboxylic acid, 1-(4-carboxyl)phenyl-3-(4-chloro)phenylpyrazoline-4,5-dicarboxylic acid, 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazine-dicarboxylic acid, 4,4'-diamino(diphenyl ether)diimidedicarboxylic acid, 4,4'-diaminodiphenylmethanediimidedicarboxylic acid, 4,4'-diamino(diphenyl sulfone)diimidedicarboxylic acid, 1,4-naphthalenedicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenedicarboxylic acid, 8-sulfo-2,3-naphthalenedicarboxylic acid, anthracene-2,3-dicarboxylic acid, 2',3'-diphenyl-p-terphenyl-4,4"-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptane-dicarboxylic acid, 5-hydroxy-1,3-benzenedicarboxylic acid, 2,5-dihydroxy-1,4-dicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxy-diphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecanedicarboxylic acid, 5,6-dehydronorbomane-2,3-dicarboxylic acid, 5-ethyl-2,3-pyridinedicarboxylic acid or camphordicarboxylic acid.

For example, a ligand may be derived from a tricarboxylic acid, such as for instance 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methyl-benzene-1,2,4-tricarboxylic acid, 3-amino-5-benzoyl-6-methylbenzene-1,2,4-tricarboxylic acid, 1,2,3-propanetricarboxylic acid or aurintricarboxylic acid.

For example, a ligand may be derived from a tricarboxylic acid, such as for instance 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3- propanetricarboxylic acid, 4,5-dihydro-4,5-dioxo-1H-pyrrolo[2,3-F]quinoline-2,7,9-tricarboxylic acid, 5-acetyl-3-amino-6-methyl-benzene-1,2,4-tricarboxylic acid, 3-amino-5-benzoyl-6-methylbenzene-1,2,4-tricarboxylic acid, 1,2,3-propanetricarboxylic acid or aurintricarboxylic acid.

For example, a ligand may be derived from a tetracarboxylic acid, such as, for instance, 1,1-dioxidoperylo[1,12-BCD]thiophene-3,4,9,10-tetracarboxylic acid, perylene-tetracarboxylic acids such as perylene-3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octane-tetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentanetetracarboxylic acids such as cyclopentane-1,2,3,4-tetracarboxylic acid.

The ligands may also be derived from a carboxylic acid selected from compounds of formula L1 to L30 and combinations thereof:

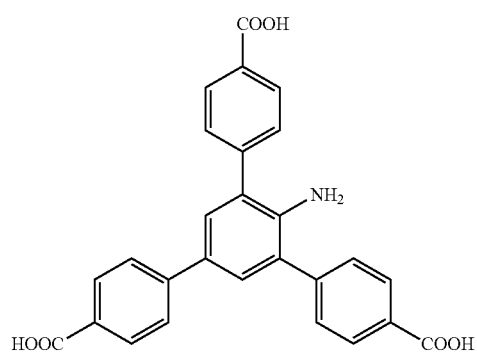
L16
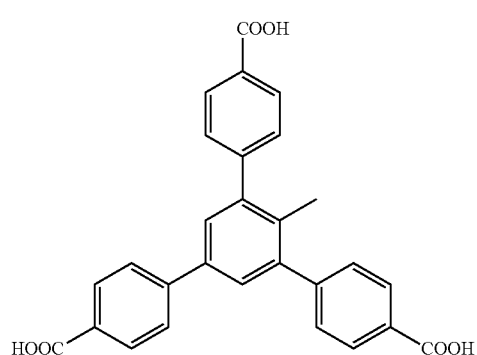
L17
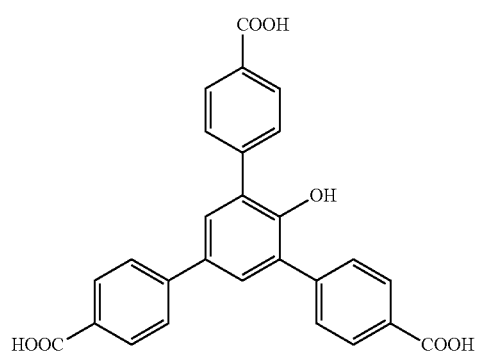
L18
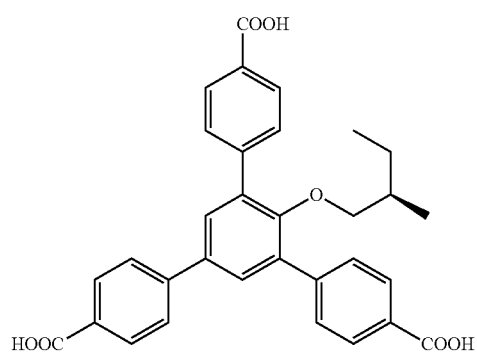
L19
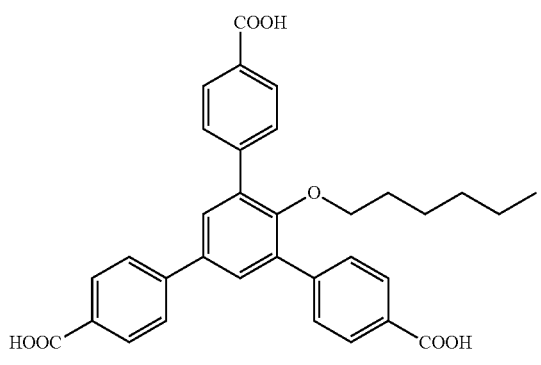
L20
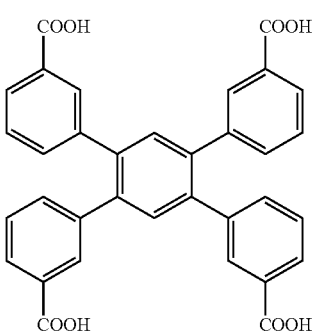
L21
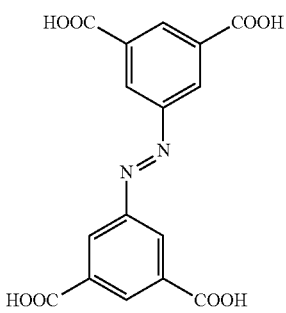
L22
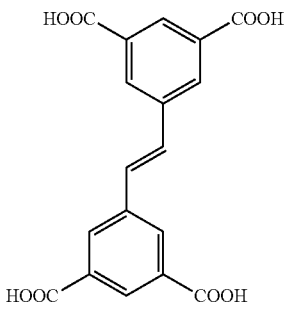
L23
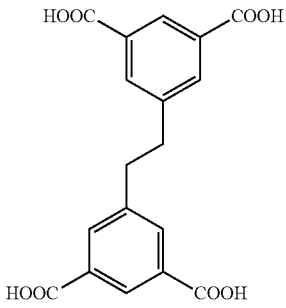
L24

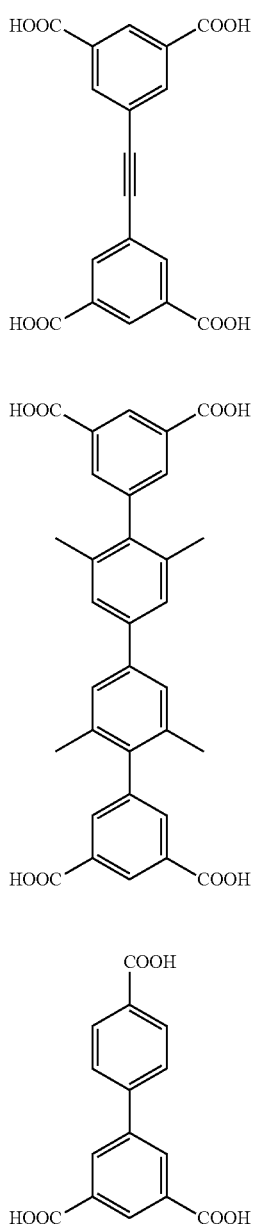
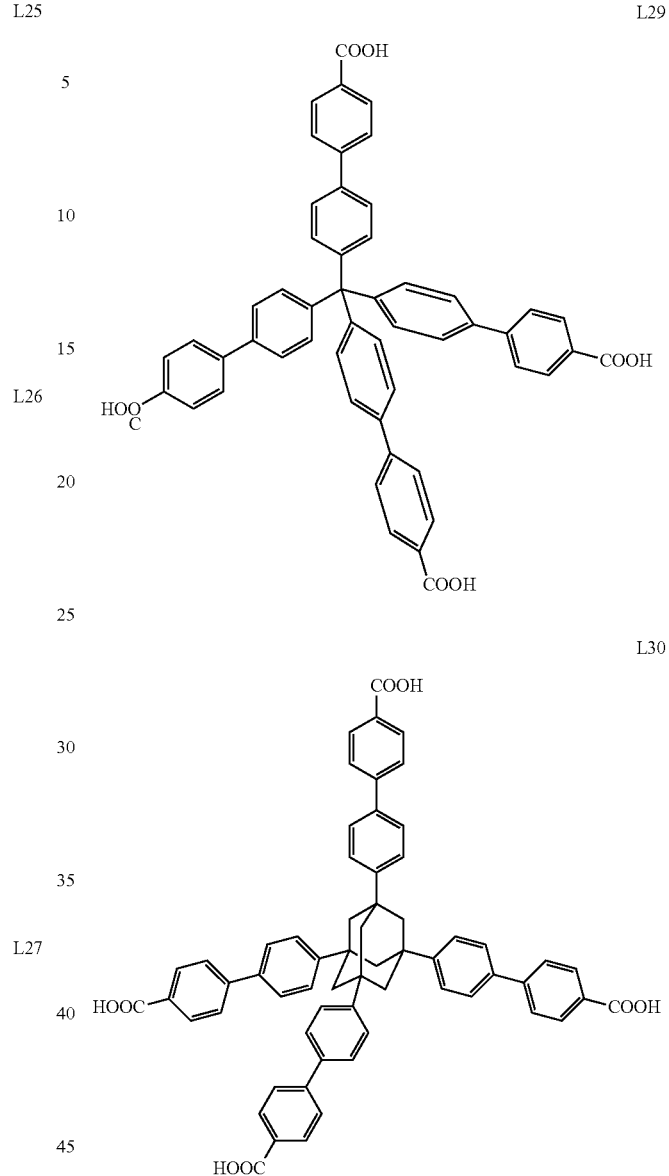
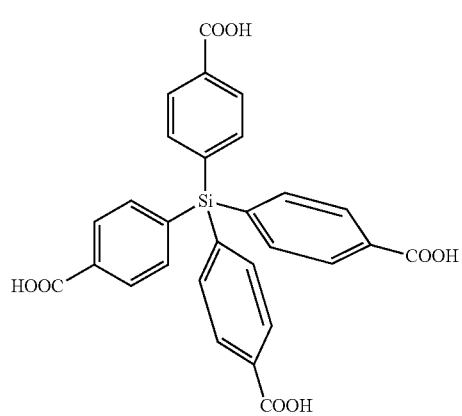
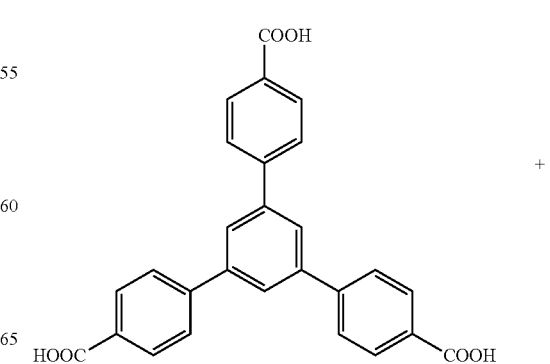
Specific combinations of ligands include ligands derived from L31 and L32:

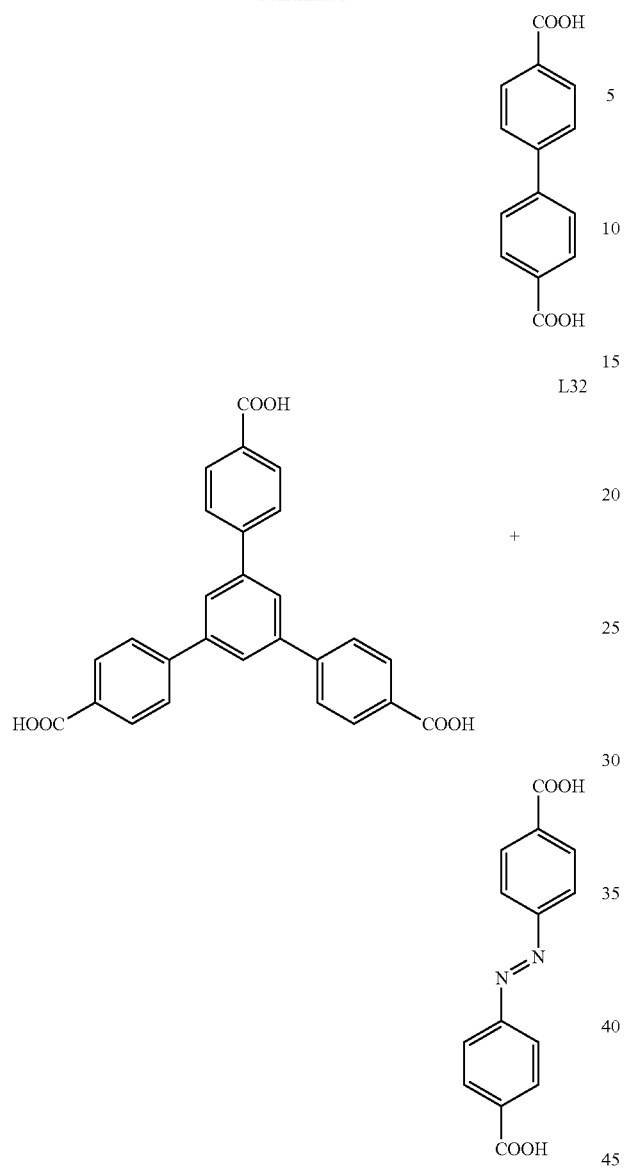
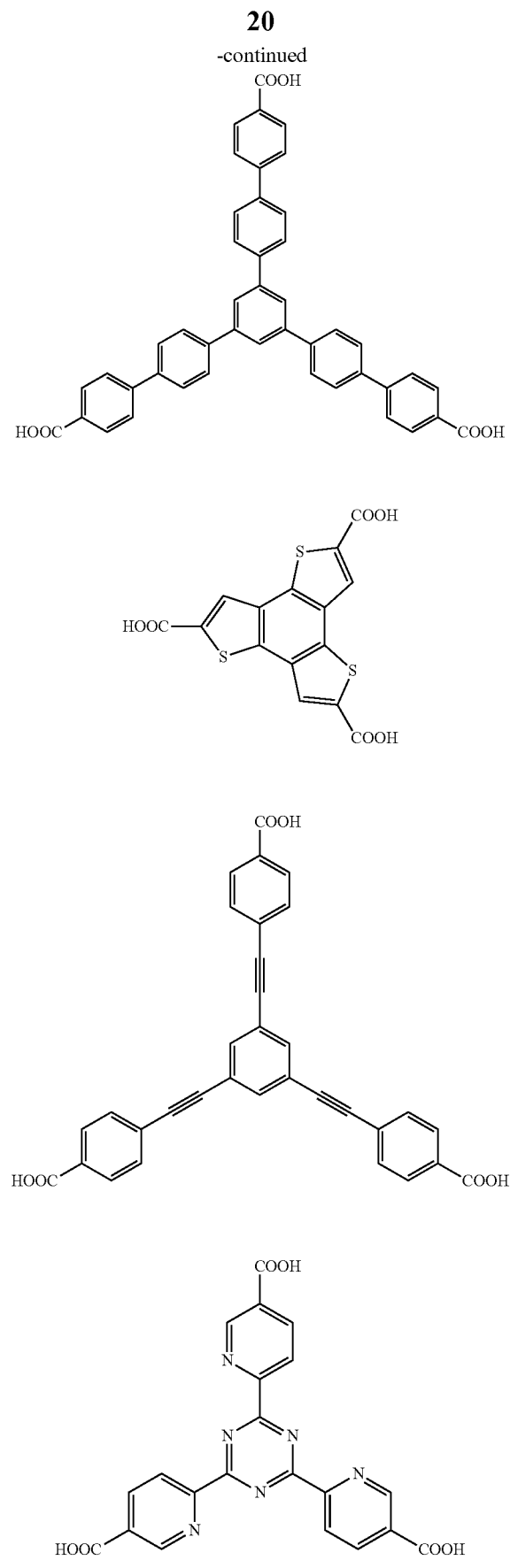
Alternatively, the ligand may be derived from a carboxylic acid selected from the following compounds or combinations thereof:

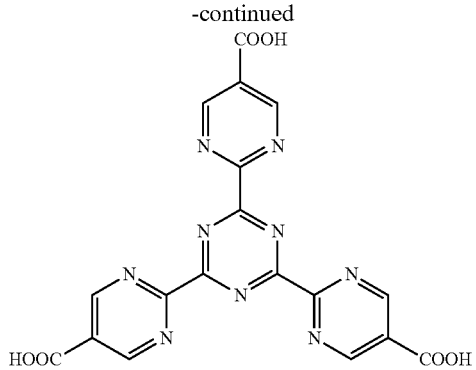

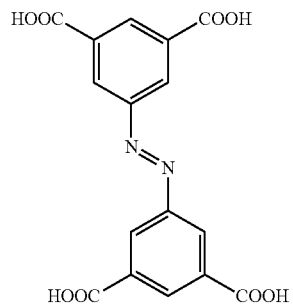

For example, the metal-organic framework may have a metal cluster of formula $Al_3O$ and comprise six ligands derived from a carboxylic acid of formula L8.

Alternatively, a metal-organic framework comprising a metal cluster having formula $Al_3O$ preferably further comprises a ligand derived from the carboxylic acids selected from:

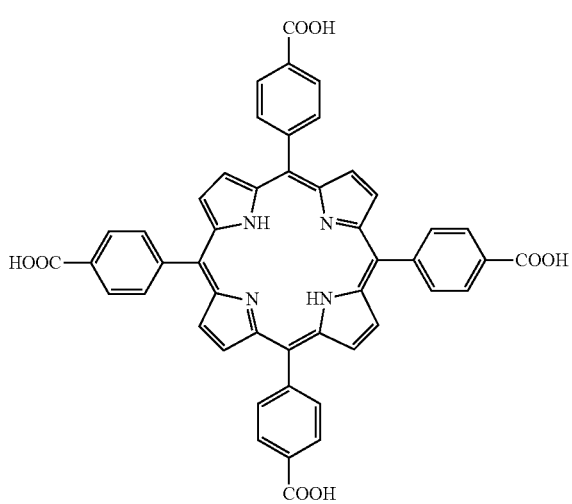

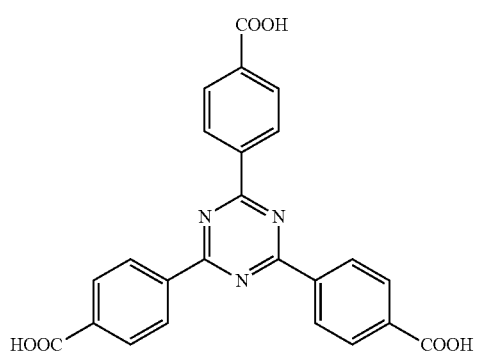

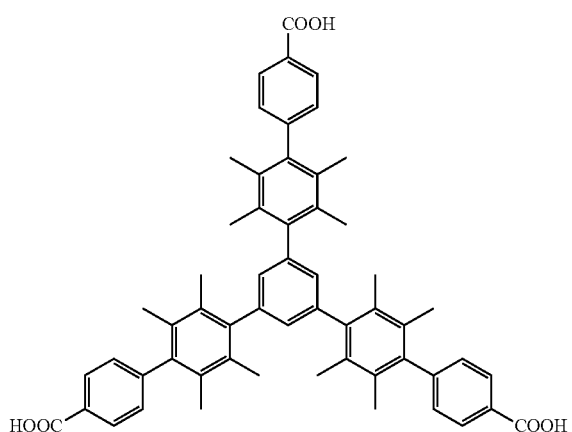

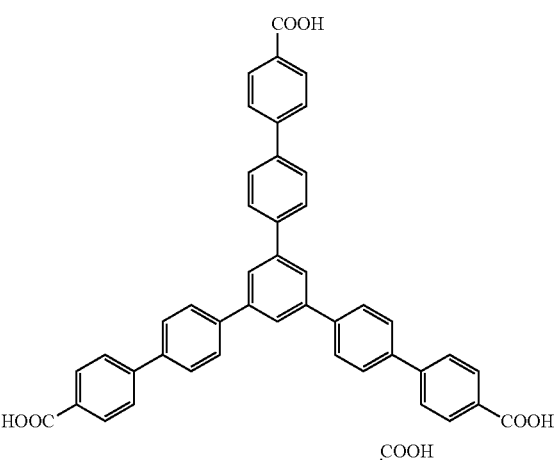

In a particular embodiment, the metal-organic framework comprises a metal cluster having formula $Al_2XO$ and one or more ligands derived from a carboxylic acid of formula L8:

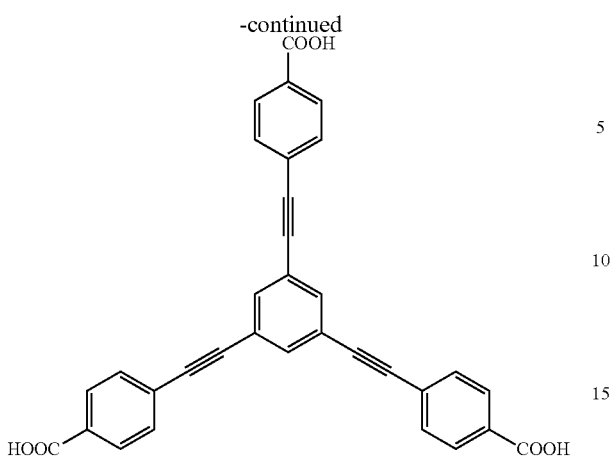

Unless otherwise specified, the crystal size may be measured as the largest dimension of the single crystal. For example, the length of the largest dimension of a crystal can be determined from a two-dimensional optical microscope image of a crystal.

Alternatively, the size may be measured as the circular equivalent (CE) diameter. For example, using a two-dimensional optical microscope image of a crystal (of any shape), the diameter of a circle with equivalent projected area can be calculated.

The specific surface area measurements were carried out by nitrogen adsorption-desorption techniques using a machine sold under the name Micrometrics ASAP 2010, on around 50 mg of material previously activated under a primary vacuum ($10^{-3}$ Torr) for 15 hours at 200° C.; the analysis being carried out by BET calculation methods.

EXAMPLES

Chemicals and Instrumentation

Unless otherwise mentioned, all the reagents were purchased and used without further purification. NMR spectra were recorded on MERCURY 300 ($^1$H 300 MHz). The following abbreviations were used to explain the multiplicities: s=singlet, d=doublet, t=triplet, q=quartet, m=multiplet, b=broad. The abbreviation for some solvent and reagent were listed here: p-Toluenesulfonate (Tos). 1,2-Dimethoxyethane (DME). tris-o-tolylphosphine (P(o-Tolyl)$_3$). N-Methyl-2-pyrrolidone (NMP). The ligands listed in Scheme S1 were purchased from Sigma Aldrich or VWR and used without further purification.

L1
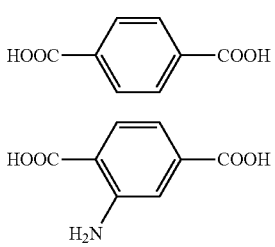

L2

L3
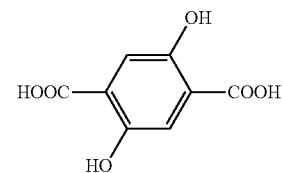

L4
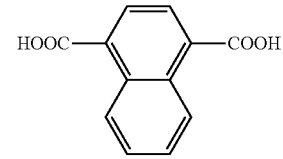

L5
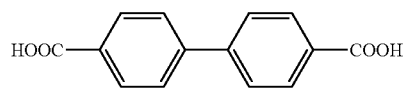

L7
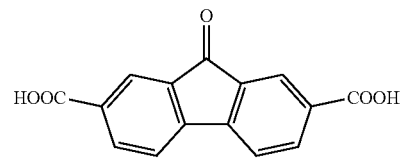

L10
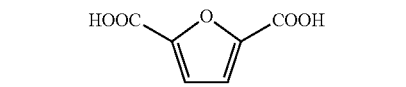

L11
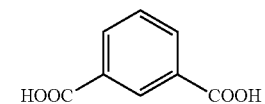

L12
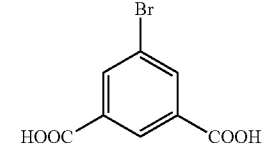

L13
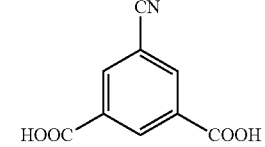

L14
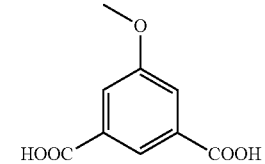

Scheme S1. Commercially Available Ligands.

To obtain the TGA data, a TGA-50 (SHIMADZU) thermogravimetric analyzer was used with a heating rate of 5° C. min−1 under N$_2$ flow. For a single crystal analysis, a pink block crystal was taken directly from the mother liquor, transferred to oil and mounted into loop. The diffraction data set was collected at 110 K on a Bruker APEX CCD diffractometer with MoKα radiation (λ=0.71609 Å). The powder X-ray diffraction patterns (PXRD) were collected on a BRUKER D8-Focus Bragg-Brentano X-ray Powder diffractometer equipped with a Cu sealed tube (λ=1.54178 Å) at a scan rate of 0.5 s deg−1. Low pressure gas adsorption measurements were performed by an ASAP 2020 with the extra-pure quality gases. High pressure excess adsorption of H2 and CH4 were measured using an automated controlled Sieverts' apparatus (PCT-Pro 2000 from Setaram) at 77 K (liquid nitrogen bath) or 298 K (room temperature).

Regarding X-ray crystallography, the data frames were collected using the program APEX2 and processed using the program SAINT routine within APEX2. The data were corrected for absorption and beam corrections based on the multi-scan technique as implemented in SADABS (G. M. Sheldrick, SHELXTL, Version 6.14, Structure Determination Software Suite, Bruker AXS, Madison, Wis., 2003). The structure was solved by direct methods using the SHELXS program of the SHELXTL package and refined by full-matrix least-squares methods with SHELXL (A. L. Spek, *PLATON*, A Multipurpose Crystallographic Tool, Utrecht University, Utrecht, The Netherlands, 1998). Metal atoms were located from the E-maps and other non-hydrogen atoms were refined with anisotropic displacement parameters during the final cycles. Hydrogen atoms were placed in calculated positions with isotropic displacement parameters set to 1.2×Ueq of the attached atom. The solvent molecules are highly disordered, and attempts to locate and refine the solvent peaks were unsuccessful. Contributions to scattering due to these solvent molecules were removed using the SQUEEZE routine of PLATON (A. L. Spek, *PLATON*, A Multipurpose Crystallographic Tool, Utrecht University, Utrecht, The Netherlands, 1998) structures were then refined again using the data generated. The contents of the solvent region are not represented in the unit cell contents in the crystal data. CCDC numbers (975771-975791 and 975820-975828) contain the supplementary crystallographic data for this paper. These data can be obtained free of charge from The Cambridge Crystallographic Data Centre via www.ccdc.cam.ac.uk/data_request/cif.

Synthesis of Ligands

Synthesis of L6 was carried out in accordance with V. K, Ol'khovik, Yu. V. Matveenko, G. V. Kalechits, A. A. Pap, and A. A. Zenyuk. Synthesis and properties of 4,4'-bis[5-alkyl (aryl)benzoxazol-2-yl]-2-hydroxy(alkoxy)biphenyls. Russian Journal of Organic Chemistry, 2006, 42, 1164-1168.

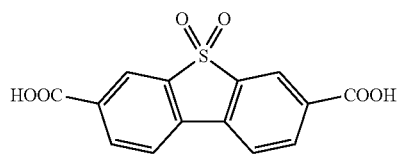

L6

Synthesis of L8 was carried out in accordance with W. Zhou, X. Yang, E. Jia, X. Wang, J. Xua, G. Ye. Ultraviolet resistance of azo-containing poly(1,3,4-oxadiazole) fibres. Polymer Degradation and Stability, 2013, 98, 691-696.

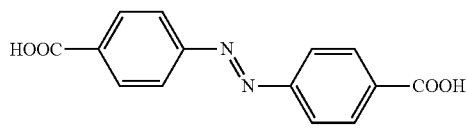

L8

Synthesis of L9 was carried out in accordance with Jiang, H.-L.; Feng, D.; Liu, T.-F.; Li, J.-R.; Zhou, H.-C., Pore Surface Engineering with Controlled Loadings of Functional Groups via Click Chemistry in Highly Stable Metal-Organic Frameworks, J. Am. Chem. Soc., 2012, 134, 14690-14693.

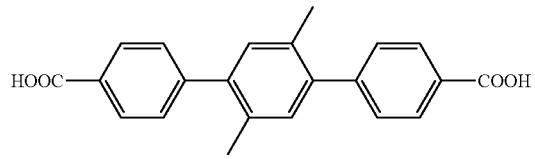

L9

Synthesis of L22 was carried out in accordance with Wang, X.-S.; Ma, S.; Rauch, K.; Simmons, J. M.; Yuan, D.; Wang, X.; Yildirim, T.; Cole, W. C.; Lopez, J. J.; de Meijere, A.; Zhou, H.-C. Metal-organic frameworks based on double-bond-coupled di-isophthalate linkers with high hydrogen and methane uptakes, Chemistry of Materials 2008, 20, 3145.

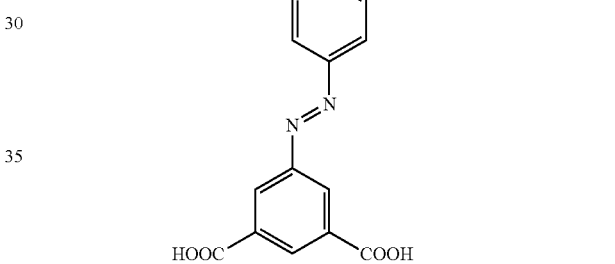

L22

Synthesis of L28 was carried out in accordance with Fournier, J.-H.; Wang, X.; Wuest, J. D. Can. Derivatives of Tetraphenylmethane and Tetraphenylsilane. Synthesis of New Tetrahedral Building Blocks for Molecular Construction. J. Chem. 2003, 81, 376-380.

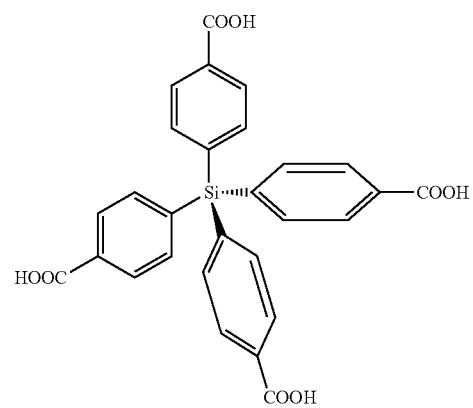

L28

Synthesis of L15

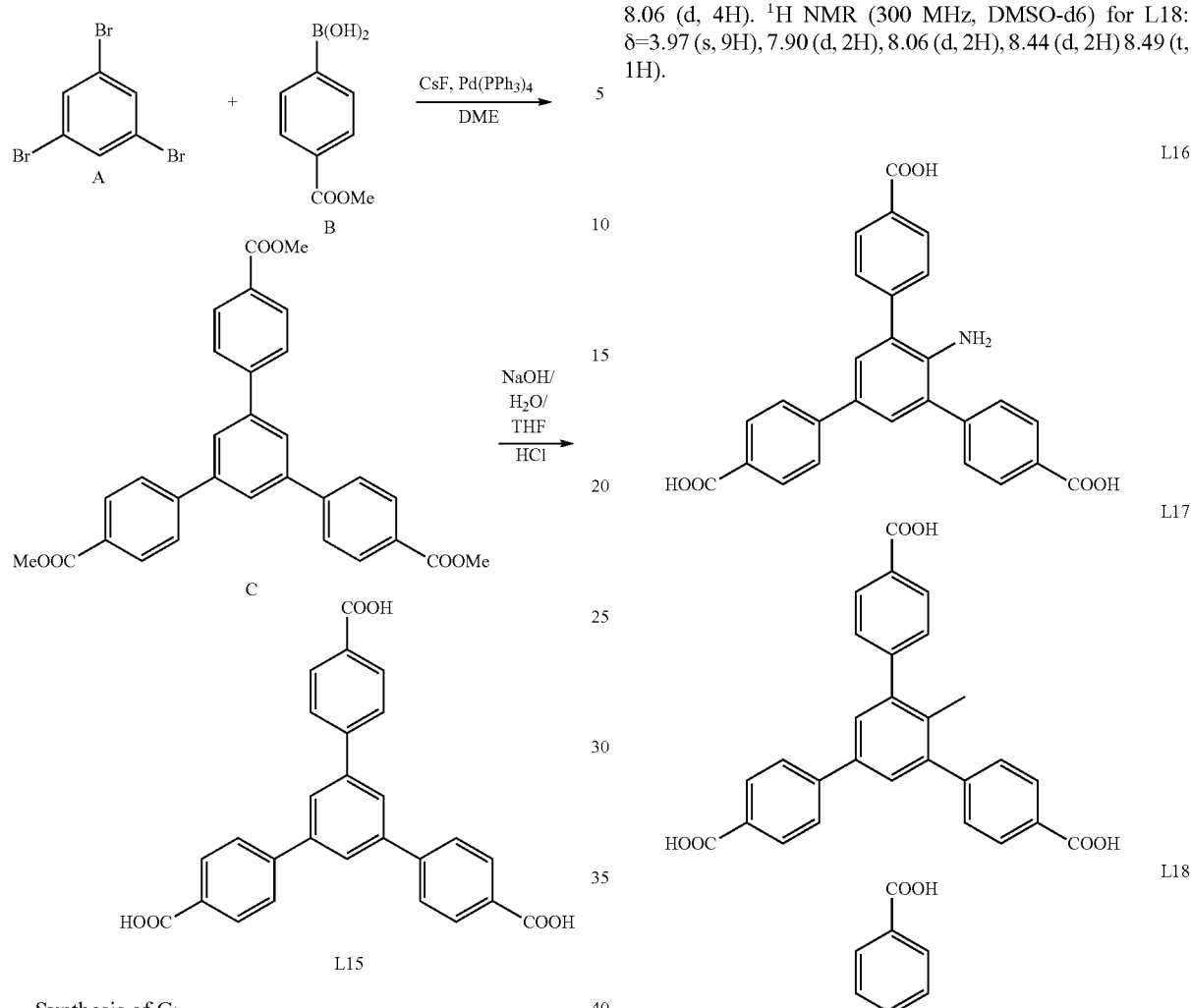

Synthesis of C:

A (2 g, 6.4 mmol), B (3.78 g, 21 mmol), CsF (3 g, 20 mmol) and Pd(PPh$_3$)$_4$ (0.2 g, 0.17 mmol) was added to a 250 mL flask, and the flask was connected to Schlenk line. 200 mL DME was degassed and added through a canula. The mixture was refluxed under the nitrogen for 48 hours. The solution was dried on rotary evaporator. 100 mL H$_2$O was added and then extract with CHCl$_3$. The residue was subjected to column chromatography on silica gel (Ethyl acetate:Hexane=20:80) to yield the title compound C as white solid 2.0 g. (Yield: 65%).

Synthesis of L15:

Compound C (2.0 g, 4.2 mmol) was suspended in 60 mL THF/MeOH (v:v=1:1), and 30 mL 10% NaOH solution was added. The mixture was stirred overnight. The pH value was adjusted to approximately 2 using hydrochloric acid. The resulting white precipitate was collected by filtration, washed with water, and dried under vacuum to give L15 (1.7 g, 92%). $^1$H NMR (CDCl$_3$): δ=3.97 (s, 9H), 7.90 (d, 2H), 8.06 (d, 2H), 8.44 (d, 2H) 8.49 (t, 1H).

Synthesis of L16, L17 and L18

L16, L17 and L18 were synthesis as the same procedure for L15 except that the starting material of 1,3,5-Tribromobenzene were replaced by 2,4,6-Tribromoaniline (for L16), 2,4,6-Tribromotoluene (for L17) and 2,4,6-Tribromophenol (for L18) respectively. $^1$H NMR (300 MHz, DMSO-d6) for L16. δ=4.74 (s, 2H), 7.52 (s, 2H), 7.74 (d, 4H), 7.85 (d, 2H), 7.98 (d, 2H), 8.10 (d, 4H). $^1$H NMR (300 MHz, yDMSO-d6) for L17. δ=2.13 (s, 3H), 7.64 (t, 6H), 7.92 (d, 2H), 8.01 (d, 2H), 8.06 (d, 4H). $^1$H NMR (300 MHz, DMSO-d6) for L18: δ=3.97 (s, 9H), 7.90 (d, 2H), 8.06 (d, 2H), 8.44 (d, 2H) 8.49 (t, 1H).

Synthesis of L19

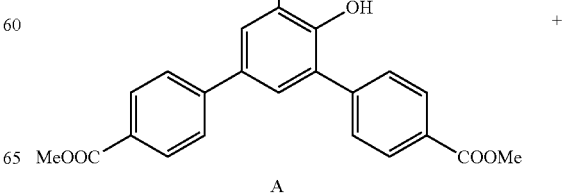

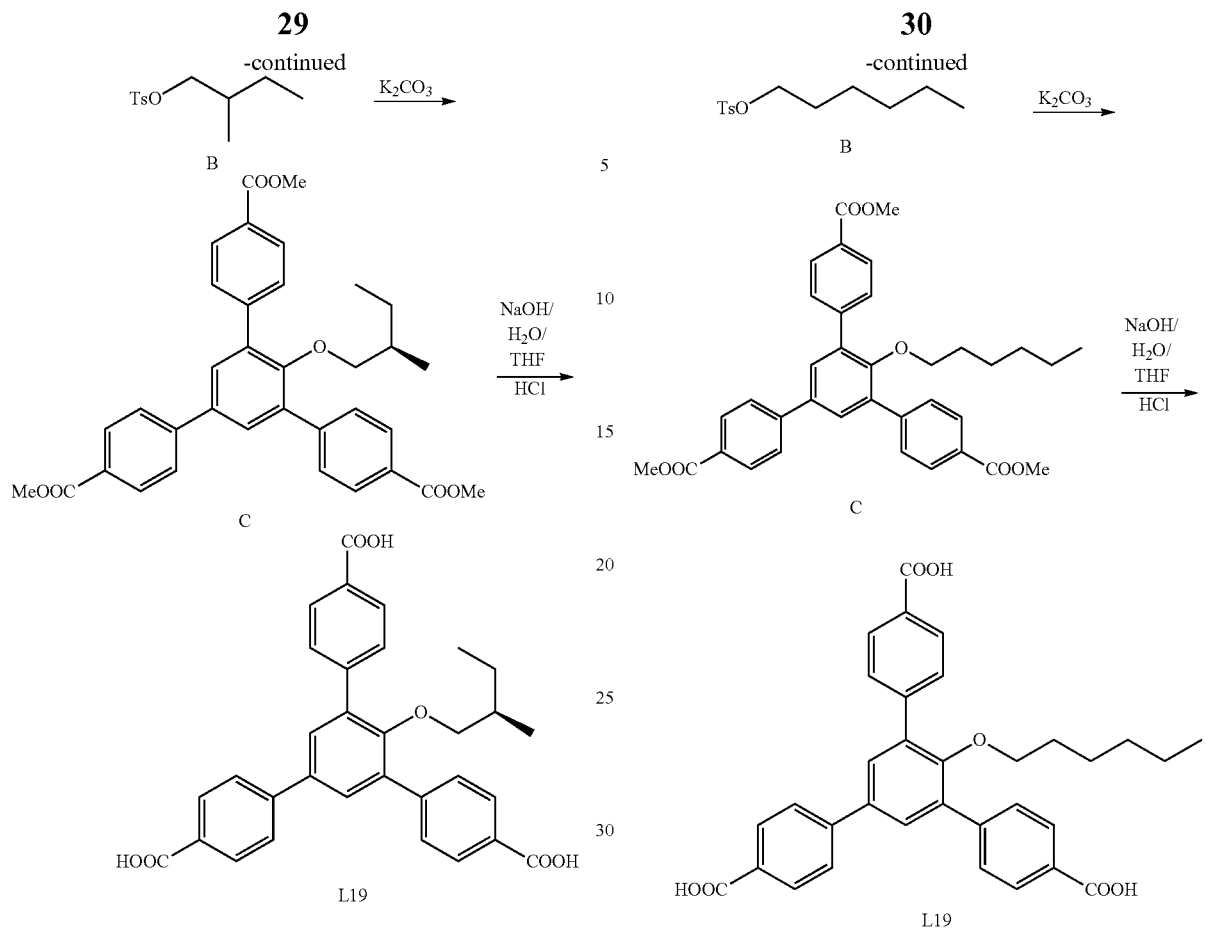

Synthesis of C:

To a round bottomed flask add A (2.0 g, 4.0 mmol), B (1.2 g, 5 mmol), K₂CO₃ (0.7 g), and DMF (30 mL). The resulting mixture was heated up to 60° C. for 12 h. After cooling to RT, ice water was added. The precipitate was collected, washed thoroughly with water, and dried to produce (2.1 g, 93%) of C. ¹H NMR (CDCl₃) for: δ=0.49 (m, 6H), 0.78 (m, 1H), 1.01 (m, 1H), 1.24 (m, 1H), 3.05 (m, 2H), 3.95 (m, 9H), 7.61 (s, 2H), 7.72 (m, 6H), 8.11 (m, 2H).

Synthesis of L19:

C (2.1 g, 3.7 mmol) was dissolved in 100 mL mixture of THF and MeOH (v/v=1/1), 50 mL 2N KOH aqueous solution was added. The mixture was stirred and refluxed overnight. The organic phase was removed. The aqueous phase was diluted to 100 mL and acidified with concentrated HCl. The precipitate was collected, washed thoroughly with water and dried to produce 1.6 g (Yield. 82.5%) of L19.

Synthesis of L20

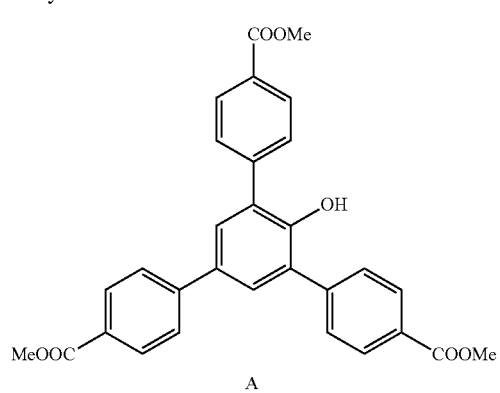

L20 was synthesized as the same procedure for L19 except the starting material B ((S)-2-Methylbutyl p-Toluenesulfonate) was replace by Hexyl p-Toluenesulfonate.

Synthesis of L21

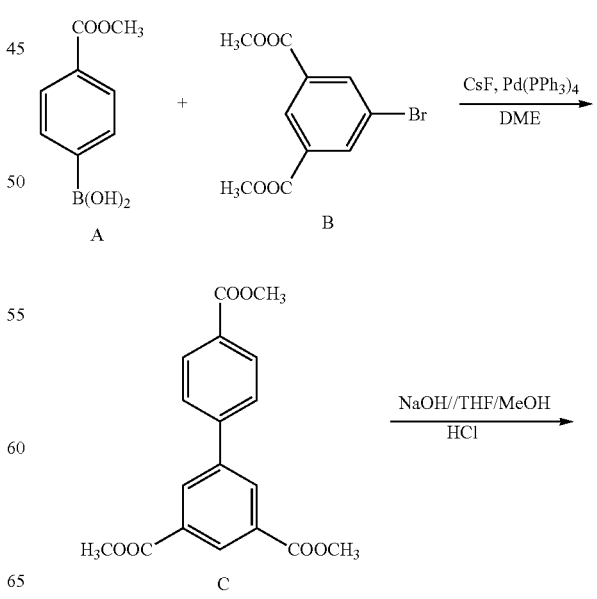

-continued

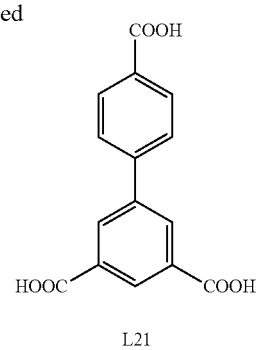

L21

Synthesis of C:

A (2 g, 11 mmol), B (2 g, 7.4 mmol), CsF (3 g, 15 mmol) and Pd(PPh$_3$)$_4$ (0.2 g, 0.17 mmol) was added to a 250 mL flask. The flask was connected to Schlenk line. 200 mL 1,2-Dimethoxyethane was degassed and added through a canula. The flask was equipped with a water condenser and refluxed under the nitrogen for 48 hours. The solution was dried on rotary evaporator. 100 mL H$_2$O was added and then extract with CHCl$_3$. The organic phase was evaporated to dryness and purified with chloroform through a short silica gel column to yield a light yellow powder 1.56 g. (Yield: 62%). $^1$H NMR (CDCl$_3$): δ=3.97 (s, 9H), 7.90 (d, 2H), 8.06 (d, 2H), 8.44 (d, 2H) 8.49 (t, 1H).

Synthesis of L21:

Compound C (1.6 g, 4.6 mmol) was suspended in 50 mL THF/MeOH (v: v=1:1), and 30 mL 10% NaOH solution was added. The mixture was stirred overnight. The pH value was adjusted to approximately 2 using hydrochloric acid. The resulting white precipitate was collected by filtration, washed with water, and dried under vacuum to give L21 (1.2 g, 91%).

Synthesis of L23 filtration and given into a NaHCO$_3$ solution. The AgBr was then removed by filtration. The solution was acidified with concentrated hydrochloric acid to give white precipitates. The solid was filtered and washed with water several times to give the product as white solid 20.5 g (Yield. 86.7%). $^1$H-NMR (DMSO-d$_6$): δ=8.23 (d, 2H), 8.40 (t, 1H).

Synthesis of C:

A solution of conc. sulphuric acid (8 ml) in methanol (30 ml) was added dropwise to a solution of B (13.2 g, 0.054 mol) in methanol (150 ml). The reaction mixture was refluxed for 20 h. After cooling to room temperature, the product was obtained as colourless crystals. After filtration, the product was washed with cold methanol to give C 11.3 g (Yield. 76.6%). $^1$H-NMR (CDCl$_3$): δ=3.96 (s, 6H), 8.35 (d, 2H), 8.6 (t, 1H).

Synthesis of D:

A 300 mL glass autoclave was charged with B (2.00 g, 7.3 mmol), Pd(OAc)$_2$ (16.4 mg, 0.0732 mmol), and P(o-Tolyl)$_3$ (44.5 mg, 0.146 mmol). The autoclave was evacuated and filled with nitrogen alternately for several times. Anhydrous triethylamine (2.2 mL, 15.8 mmol) and anhydrous NMP (2.2 mL) were added under nitrogen. The autoclave was evacuated, filled with 1.5 bar of ethane. The pressure was released, and then built up again, and this release and repressurization was repeated three more times in order to saturate the solvent with ethene. The contents of the autoclave were then kept under a pressure of 1.5 bar of ethene and stirred at 100° C. for 25.5 h. After having been cooled down to ambient temperature, the autoclave valve was opened to release excess ethene, and the mixture was taken up in methylene chloride (100 mL). The solution was washed with water (3×50 mL), dried MgSO$_4$, and concentrated under reduced pressure. The residue was subjected to column chromatography on silica gel to yield 1.181 g (78%) of the title compound as a light yellow solid. $^1$H NMR (250 MHz, CDCl$_3$): δ=3.98 (s, 12H), 7.31 (s, 2H), 8.38 (d, 4H), 8.59 (t, 2H).

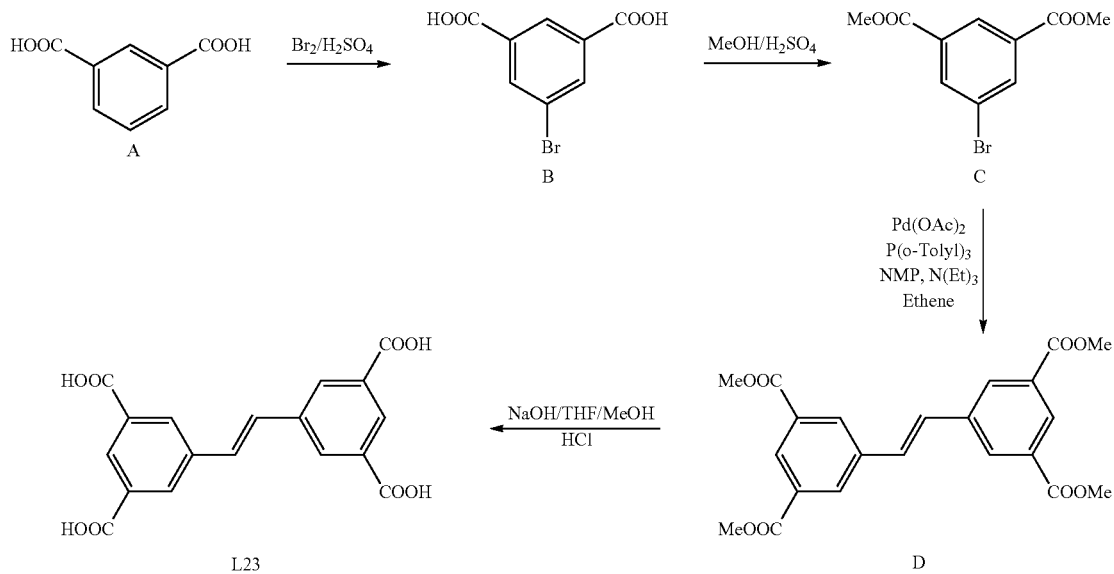

Synthesis of B:

A mixture of A (12.2 g, 73.5 mmol), Ag$_2$SO$_4$ (13.3 g, 43 mmol) and Br$_2$ (5 ml, 97 mmol) in conc. sulphuric acid was stirred at 60° C. for 32 h. The excess of Br$_2$ was removed by addition of saturated Na$_2$S$_2$O$_3$ solution very slowly. The residue was poured into ice-water. The solids were isolated by Synthesis of L23:

D (3 g, 7.3 mmol) was suspended in 100 mL THF/MeOH (v: v=1:1), and 20 mL 10% NaOH solution was added. The mixture was stirred overnight. The pH value was adjusted to approximately 2 using hydrochloric acid. The resulting white precipitate was collected by filtration, washed with water, and dried under vacuum to give L23 2.46 g (Yield. 95%).

Synthesis of L24

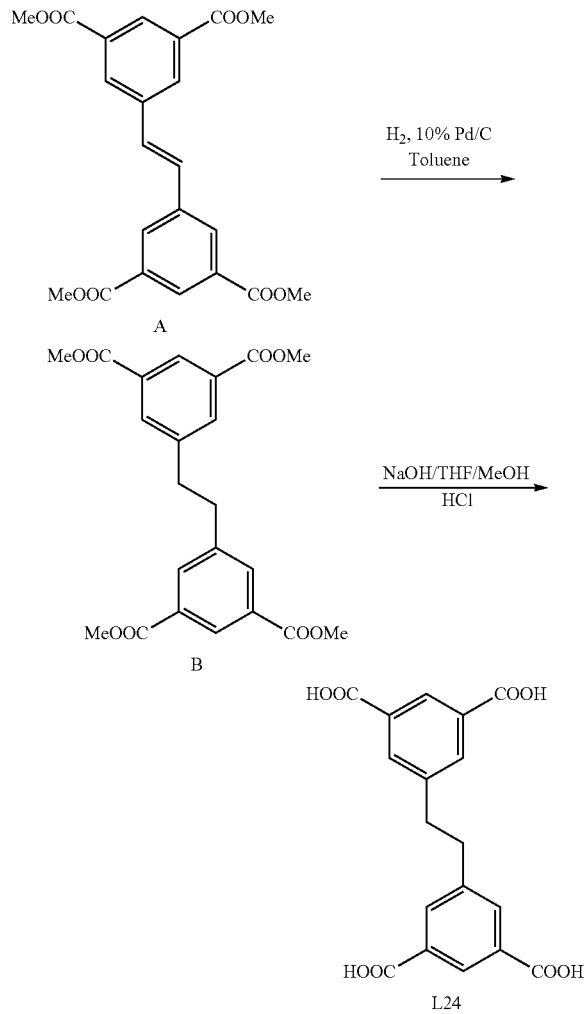

Synthesis of B:

A was synthesized as the same way for D in L23. A mixture of compound A (170 mg, 0.412 mmol), 10% Pd/C (54 mg) and toluene (30 mL) was hydrogenated at 50° C. ($H_2$, 3 bar) for 4 h. The catalyst was filtered off through a pad of Celite and then washed with chloroform. The filtrate was evaporated to dryness on rotary evaporator. The residue was recrystallized from chloroform/toluene to give 152 mg of B as colorless solid (Yield. 89%). $^1$H-NMR (300 MHz, CDCl$_3$): δ=3.02 (s, 4H), 3.91 (s, 12H), 8.01-8.03 (m, 4H), 8.49-8.52 (m, 2H).

Synthesis of L24:

Compound C (130 mg) was suspended in 50 mL THF/MeOH (v: v=1:1), and 3 mL 10% NaOH solution was added. The mixture was stirred overnight. The pH value was adjusted to approximately 2 using hydrochloric acid. The resulting white precipitate was collected by centrifuge, washed with water, and dried under vacuum to give L24 (100 mg, 92%). $^1$H-NMR (DMSO-d$_6$): δ=13.10 (s, br, 4H), 8.29 (s, 2H), 8.04 (s, 4H), 3.02 (s, 2H).

Synthesis of L25

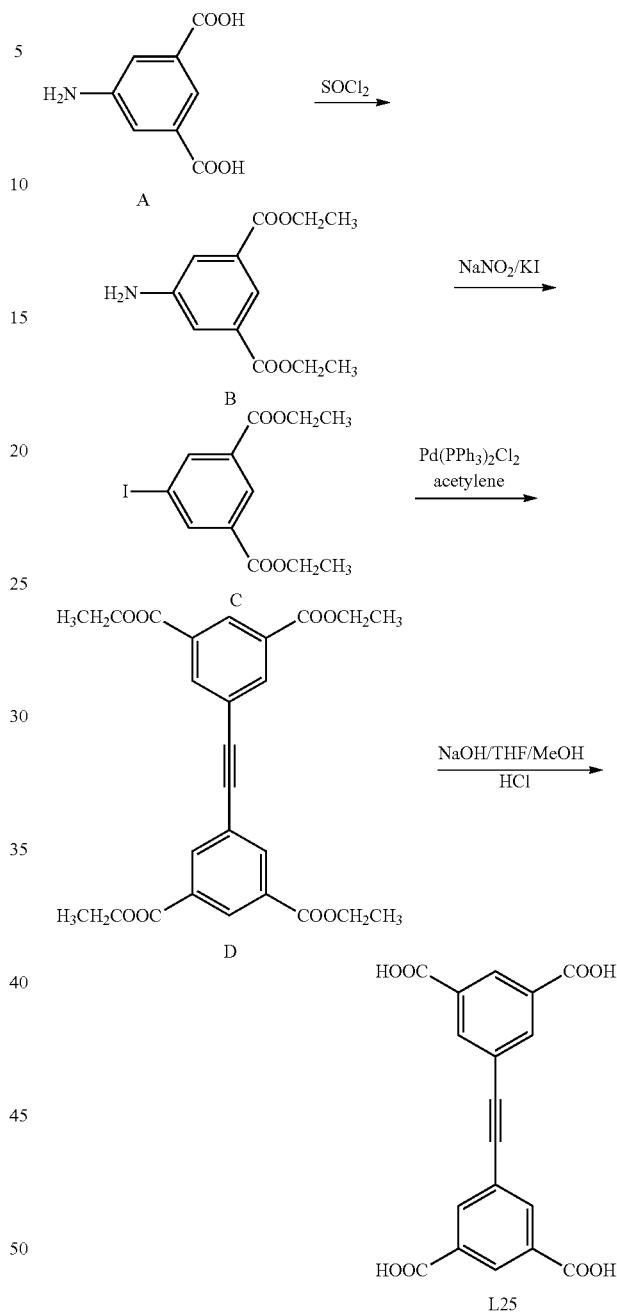

Synthesis of B:

12 mL SOCl$_2$, (165 mmol) was slowly added to a stirred solution of A (10 g, 60 mmol) in 100 mL of absolute EtOH. After stirring under reflux for 5 hours, there are a lot of precipitates formed. The solvent was removed and the crude product was washed with a saturated aqueous solution of Na$_2$CO$_3$. After filtered, the solid was dried at 60° C. overnight to give B as white solid of 12.8 g (Yield. 90%). $^1$H NMR (CDCl$_3$): δ=1.4 (t, 3H), 4.3 (q, 2H), 7.5 (s, 2H), 8.1 (s, 1H).

Synthesis of C:

A solution of NaNO$_2$ (2.32 g) in 20 mL water was added to a cloudy mixture of B (6.6 g, 27.8 mmol) in 30 mL 2M hydrochloric acid at 0° C. The mixture changed to clear solution slowly. After stirred at 0° C. for 45 minutes, an ice-cold KI aqueous solution was added. Then mixture changed to dark red and sticky. After 100 mL CH$_2$Cl$_2$ was added, the mixture was allowed to stir at RT for 4 hours. The aqueous phase was washed with CH$_2$Cl$_2$ three times. The combined organic phases were dried with MgSO$_4$. After the solvent was removed, the crude product was purified by column chromatography with CH$_2$Cl$_2$ as the eluent. $^1$H NMR (Acetone): δ=1.4 (t, 3H), 4.4 (q, 2H), 8.2 (s, 2H), 8.6 (s, 1H).

Synthesis of D:

C (7.3 g, 20.9 mmol), Pd(PPh$_3$)$_2$Cl$_2$ (0.2 g). CuI (0.1 g) were dissolved in 200 mL Et$_2$NH under nitrogen atmosphere. The mixture was bubbled with acetylene for 8 hours at RT, and then stirred overnight. The solvent was removed and the residual powder was dissolved in CH$_2$Cl$_2$ (300 mL) and 200 mL hydrochloric acid (2M). The aqueous phase was extracted with CH$_2$Cl$_2$ twice. The mixed organic phase was washed with water twice and dried with Na$_2$SO$_4$. After the solvent was removed, the crude product was purified by column chromatography with CH$_2$Cl$_2$ as eluent to give the product as pale-yellow powder. $^1$H NMR (CHCl$_3$): δ=1.5 (t, 3H), 4.4 (q, 2H), 8.4 (s, 2H), 8.7 (s, 1H).

Synthesis of L25:

D was suspended in 100 mL THF, to which was added 20 mL 2 M KOH aqueous solution. The mixture was refluxed under N$_2$ overnight. THF was removed on rotary evaporator and diluted hydrochloric acid was added into the aqueous solution until the solution became acidic. The solid was collected by filtration, washed with water several times and dried in the air.

Synthesis of L26

Synthesis of B:

A solution of NaNO$_2$ (2.32 g) in 20 mL water was added to a cloudy mixture of A (6.6 g, 27.8 mmol) in 30 mL 2M hydrochloric acid at 0° C. After stirred at 0° C. for 45 minutes, an ice-cold KI aqueous solution was added. Then mixture changed to dark red and sticky. After 100 mL CH$_2$Cl$_2$ was added, the mixture was allowed to stir at RT for 4 hours. The aqueous phase was washed with CH$_2$Cl$_2$ three times. The combined organic phases were dried with MgSO$_4$. After the solvent was removed, the crude product was purified by column chromatography with Ethyl acetate: Hexans=4:1 as the elute. (8.8 g, Yield. 91%) $^1$H NMR (Acetone): δ=1.4 (t, 3H), 4.4 (q, 2H), 8.2 (s, 2H), 8.6 (s, 1H).

Synthesis of D:

Degassed dry DMF (18 mL) was added to a mixture of B (3.48 g, 10 mmol), C (3.1 g, 12 mmol), potassium acetate (2.2 g, 24 mmol), and Pd(OAc)$_2$ (49 mg, 0.22 mmol). The mixture was heated to 90° C. (oil bath) for 24 h. After cooling to room temperature, the solution was added dropwise to water (90 mL) and stirred vigorously for 10 min. The solid was collected by filtration and purified through column chromatography on silica gel (hexane/ethyl acetate, 80:20, second point) to afford product as a white solid (2.01 g, 86%). $^1$H NMR (CDCl$_3$): δ=1.346 (s, 12H), 1.396 (t, 6H), 4.39$^2$ (q, 4H), 8.600 (d, 2H), 8.739 (t, 1H).

Synthesis of F:

A solution of NaNO$_2$ (2.32 g) in 20 mL water was added to a cloudy mixture of E (6.6 g, 27.8 mmol) in 30 mL 2M hydrochloric acid at 0° C. After stirred at 0° C. for 45 minutes, an ice-cold KI aqueous solution was added. Then mixture changed to dark red and sticky. After 100 mL CH$_2$Cl$_2$ was

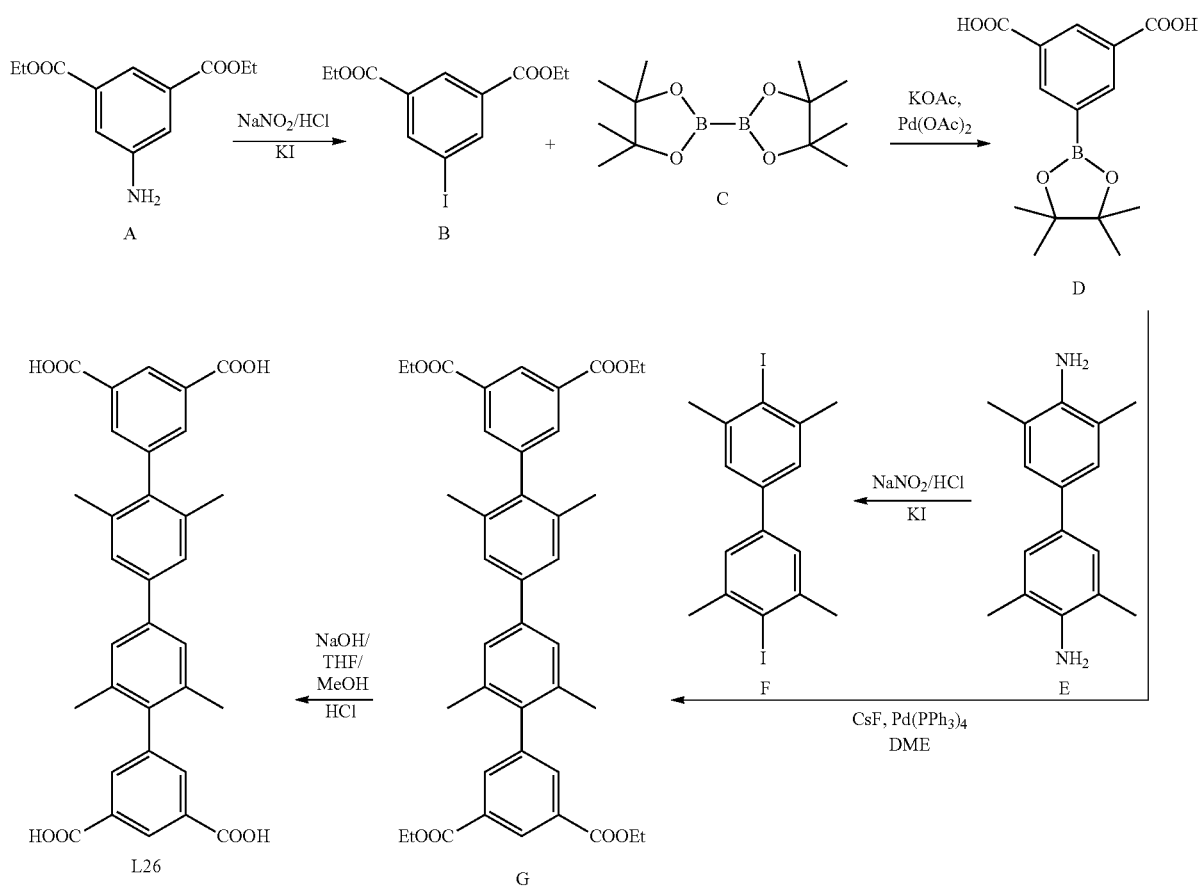

added, the mixture was allowed to stir at RT for 4 hours. The aqueous phase was washed with CH₂Cl₂ three times. The combined organic phases were dried with MgSO₄. After the solvent was removed, the crude product was purified by column chromatography with Ethyl acetate: Hexane=4:1 as the eluent. ¹H NMR (CDCl₃): δ=2.538 (s, 12H), 7.261 (s, 4H).

Synthesis of L26:

A 250-mL Schlenk flask was charged with of D (0.8 g, 3.05 mmol), F (3.7 g 8 mmol), CsF (4 g, 26.4 mmol), and 0.2 g of Pd(P(Ph)₃)₄. 120 ml of DME was degassed and transferred. A water condenser was then equipped and the flask was heated to reflux under the nitrogen for 72 hours. The solvent was dried on rotary evaporator. The residue was dissolved by CH₂Cl₂ and purified by column chromatography to white crystal. The white crystal was dissolved in a 500-mL Schlenk flask with 200 mL mixture of THF and MeOH (v/v=1:1). 100 mL of 0.3M NaOH aqueous solution was added. The flask was heated to reflux overnight. The solution is then acidified by diluted hydrochloric acid to give white precipitate, which was filtered and washed with water several times to get L26 1.2 g (Yield. 68%). ¹H NMR (DMSO): δ=2.051 (s, 12H), 7.516 (s, 4H), 7.925 (d, 4H), 8.490 (t, 2H).

Synthesis of L27

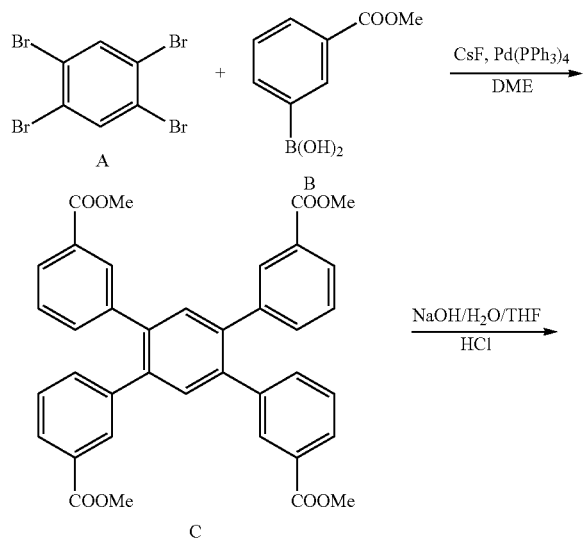

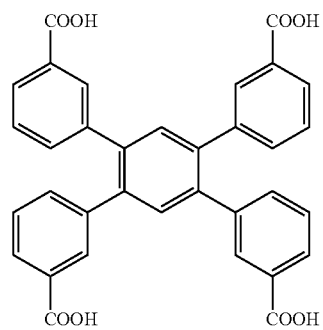

L27

Synthesis of C:

A 250-mL Schlenk flask was charged with of A (1.2 g, 3.05 mmol), B (3.28 g 18.30 mmol), CsF (4 g, 26.4 mmol), and 0.2 g of Pd(P(Ph)₃)₄. 120 ml DME was degassed and transferred. A water condenser was then equipped and the flask was heated to reflux under the nitrogen for 72 hours. The solvent was dried on rotary evaporator. The residue was dissolved by CH₂Cl₂ and purified by column chromatography to white crystal.

Synthesis of L27:

The white crystal was dissolved in a 500 mL Schlenk flask with 200 mL mixture of THF and MeOH (v/v=1:1). 100 mL of 0.3M NaOH aqueous solution was added. The flask was heated to reflux overnight. The solution is then acidified by diluted hydrochloric acid to give white precipitate of C, which was filtered and washed with water several times to get L27 1.2 g (Yield. 68%). ¹H NMR (DMSO): δ=12.9 (s, 4H), 7.83 (t, 4H), 7.80 (s, 4H), 7.55 (s, 2H), 7.45 (d, 4H), 7.40 (d, 4H).

Synthesis of L29

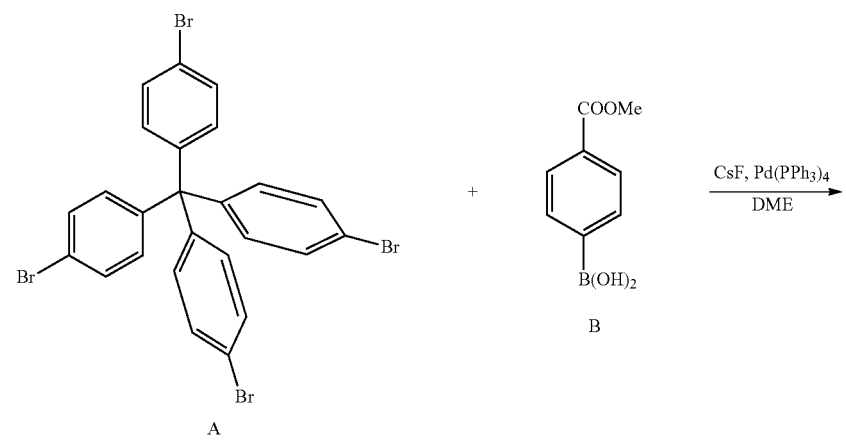

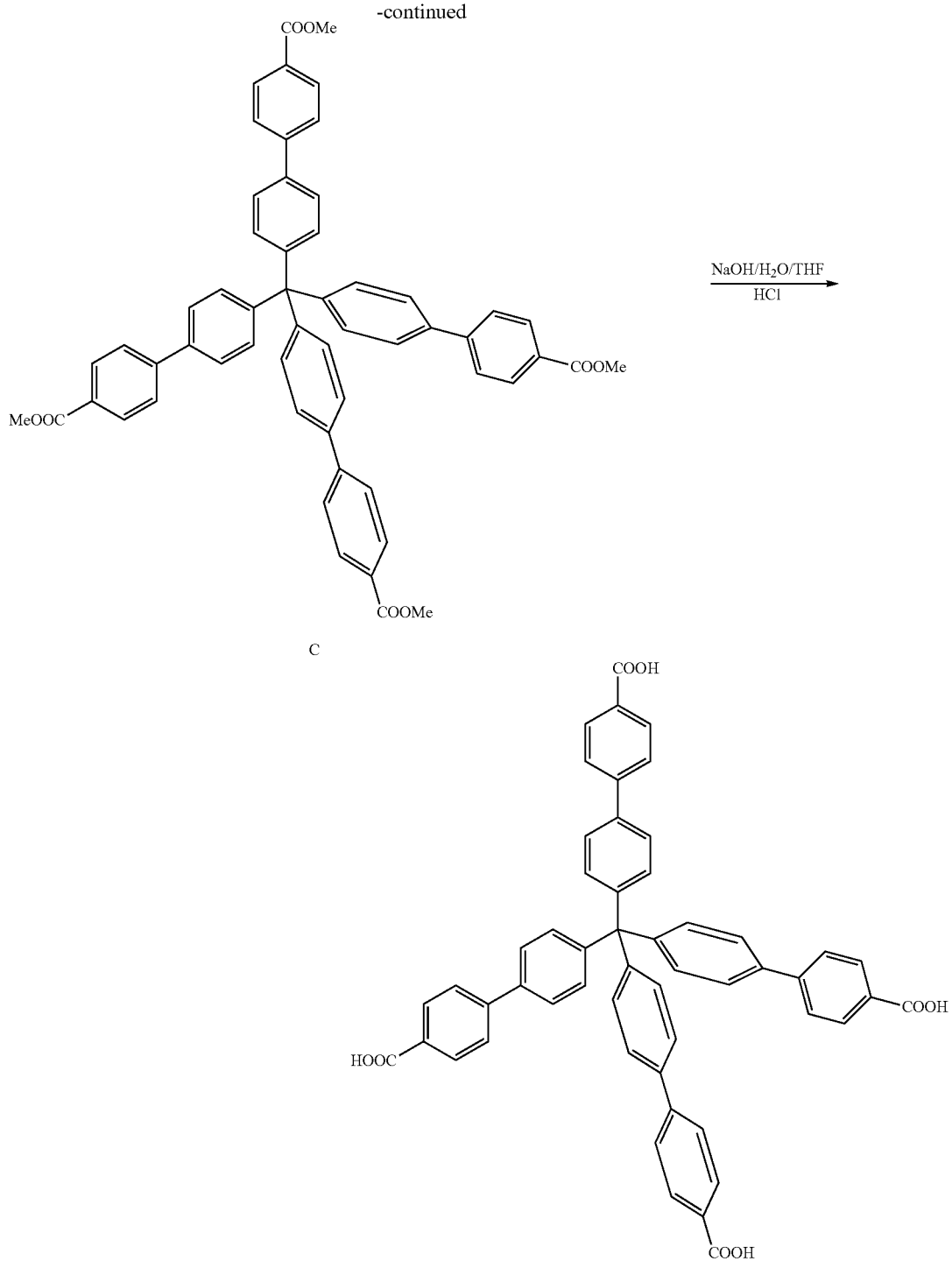

Synthesis of C:

B is prepared according to the procedure described in reference 5.

A 250 mL Schlenk flask was charged with A (4 g, 6.3 mmol), B (6.79 g, 37.7 mmol), CsF (9.5 g, 63.9 mmol), and Pd(P(Ph)$_3$)$_4$ 0.3 g. 120 ml DME was degassed and transferred. A water condenser was then equipped. The flask was heated to reflux under the nitrogen for 48 hours. The solvent was dried on rotary evaporator. The residue was dissolved by CH$_2$Cl$_2$, and purified by column chromatography to get C 4.1 g (Yield. 76%).

Synthesis of L29:

C (4.1 g, 4.8 mmol) was dissolved in a 500 mL Schlenk flask with 200 mL mixture of THF and MeOH (v/v=1:1). 100 mL of 1.25M NaOH aqueous solution was added. The flask was heated to reflux overnight. The solution is then acidified by diluted hydrochloric acid to give white precipitate, which was filtered and washed with water and acetone several times. $^1$HNMR (DMSO): δ=12.93 (s, 4H), 7.99 (d, 8H), 7.81 (d, 8H), 7.76 (d, 8H), 7.41 (d, 8H).

Synthesis of L30 ferred. A water condenser was then equipped. The flask was heated to reflux under the nitrogen for 48 hours. The solvent was dried on rotary evaporator. The residue was dissolved by $CH_2Cl_2$, and purified by column chromatography to get C 2.9 g (Yield. 76%).

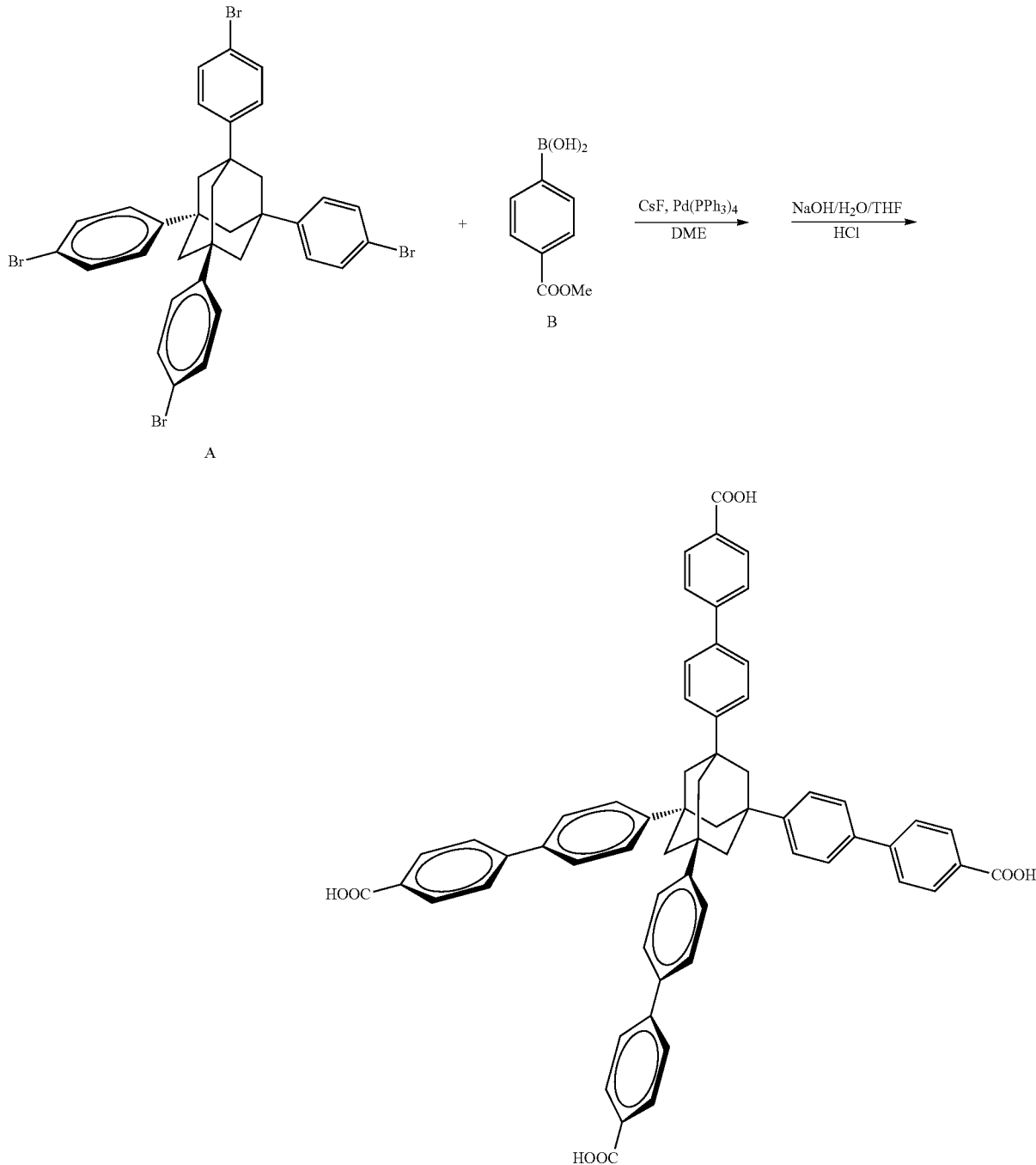

Synthesis of C:

B is prepared according to the procedure described in reference 1. A 250-mL Schlenk flask was charged with A (3 g, 4.0 mmol), B (4.2 g, 24 mmol), CsF (9.5 g, 63.9 mmol), and Pd(P(Ph)$_3$)$_4$ 0.3 g. 120 ml of DME was degassed and trans- Synthesis of L30:

C (2.9 g, 3.0 mmol) was dissolved in a 500 mL Schlenk flask with 200 mL mixture of THF and MeOH (v/v=1:1). 100 mL of 1.25 M NaOH aqueous solution was added. The flask was heated to reflux overnight. The solution is then acidified by diluted hydrochloric acid to give white precipitate, which was filtered and washed with water and acetone several times. $^1$H NMR (CDCl$_3$): δ=2.29 (s, 8H), 3.92 (s, 12H) 7.64 (m, 6H) 8.08 (d, 2H).

The structures shown in the examples below represent the ligands employed which replace the (CH$_3$COO) ligands seen in the starting material whilst retaining the same metal ion cluster.

Example 1

Synthesis of Al$_3$O(ABTC)$_6$-PCN 250 (Al)

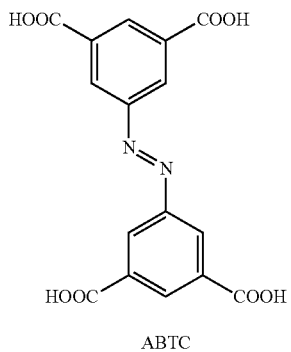 [SMILES: O=C(O)c1cc(/N=N/c2cc(C(=O)O)cc(C(=O)O)c2)cc(C(=O)O)c1]

ABTC 10 mg of [Al$_3$O(OOCCH$_3$)$_6$.3CH$_3$CN][AlCl$_4$] and 10 mg of ABTC were dissolved in 2 ml of DMF, then 0.5 ml of acetic acid was added. The solution was sealed in a 4 ml vial and put into oven at 150° C. for 5 days. After cooling down to room temperature, light yellow crystals were harvested.

Figure 2:
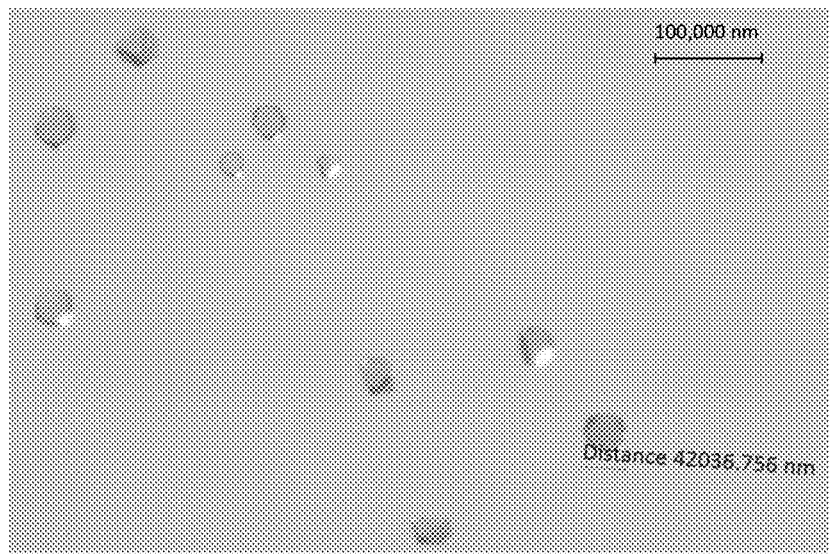
FIGS. 2 to 4 show microscope images of PCN-250 (Al), (Example 1).
Figure 3:
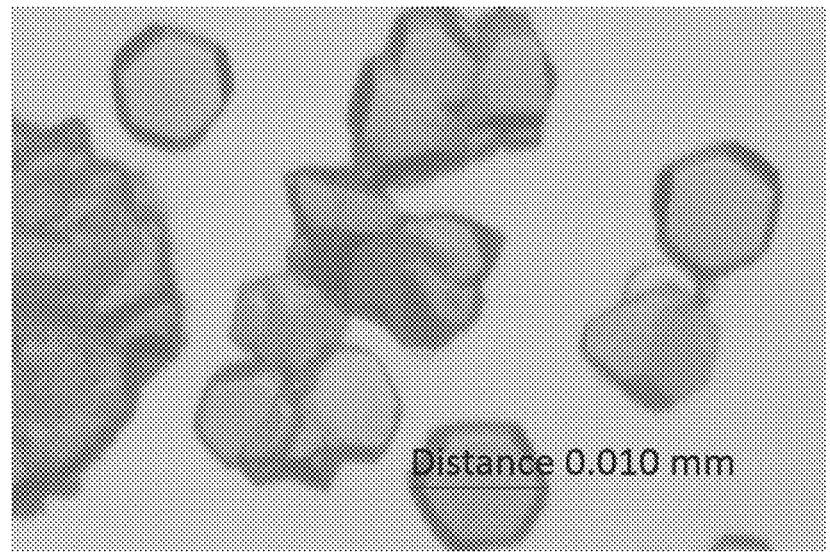
Figure 4:

Optical microscope images of PCN-250 (Al) (Example 1) are shown in FIGS. 2-4. Crystal sizes of 42 μm, 10 μm, and 72 μm respectively were observed.

The crystal data and structure refinements for a single crystal of PCN-250 (Al) (Example 1) are shown in Table 1.

TABLE 1

|  | PCN-250-Al |
| --- | --- |
| Formula | C$_9$ H$_6$ Al O$_{5.33}$ |
| Formula weight | 226.45 |
| Crystal Color/Shape | Light Yellow Block |
| Crystal System | Cubic |
| Space Group | P43n |
| a (Å) | 21.6035(10) |
| V (Å$^3$) | 10082.60(8) |
| Z | 24 |
| d$_{calcd.}$ (g/cm$^3$) | 0.895 |
| μ(mm$^{-1}$) | 0.121 |
| F(000) | 2776 |
| θ$_{max}$ [deg] | 26.37 |
| Completeness | 98.8% |
| Collected reflections | 3427 |
| Unique reflections | 3238 |
| Parameters | 145 |
| Restraints | 3 |
| R$_{int}$ | 0.0308 |
| R1[I > 2σ(I)] | 0.0386 |
| wR2 [I > 2σ(I)] | 0.1241 |
| R1 (all data) | 0.0408 |
| wR2 (all data) | 0.1254 |
| GOF on F$^2$ | 1.136 |
| Δρ$_{max}$/Δρ$_{min}$ [e.Å$^{-3}$] | 0.371/−0.250 |

RESULTS & TESTING

Gas Adsorption Measurement for PCN-250 (Al):

The adsorption characteristics of PCN-250 (Al) were measured.

Before measurements were carried out, as-synthesized PCN-250 (Al) samples were washed with dry DMF several times, and immersed in DMF for 2 days to remove unreacted starting ligands, inorganic species and acetic acid. After that, DMF was decanted, washed with dry methanol several times, and immersed in methanol at 65° C. This was repeated for 2 days to completely substitute the coordinating molecule. After that, methanol was decanted, the sample was washed with dry CH$_2$Cl$_2$ several times, and CH$_2$Cl$_2$ solvent exchange was conducted under a well-sealed vial at 60° C. for 3 days. After that, the solvent was removed on a vacuum line and the sample was transported in a glove box to prevent the re-adsorption of H$_2$O from the air. The sample was then activated again using the 'outgas' function of the adsorption instrument for 12 h at 190° C. Gas adsorption was then measured.

Figure 5:
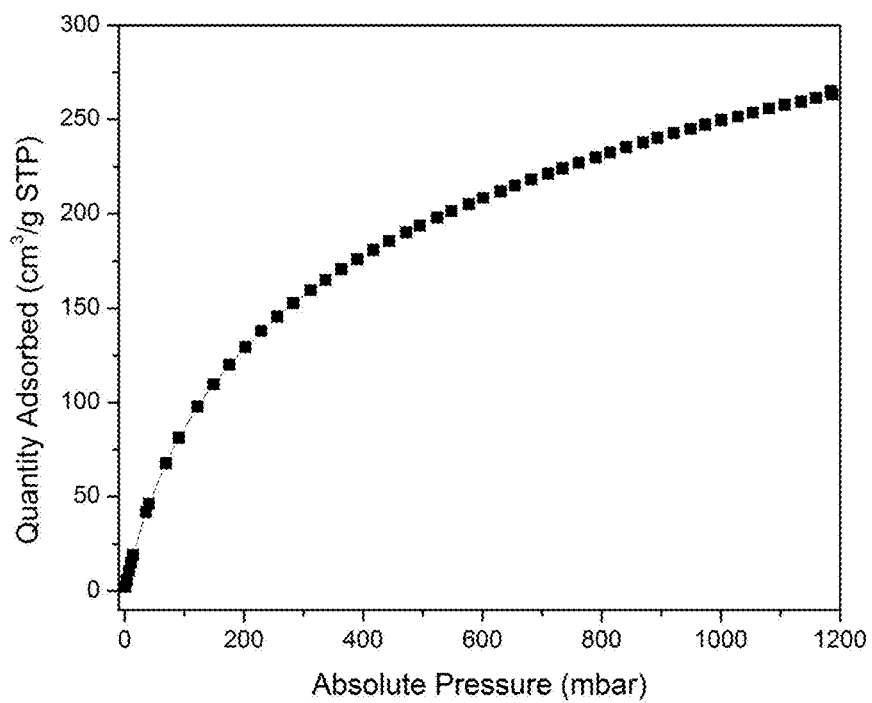
FIG. 5 shows the $H_2$ uptake (adsorption) measured for PCN-250 (Al).

FIG. 5 shows the H$_2$ uptake (adsorption) measured for PCN-250 (Al).

Figure 6:
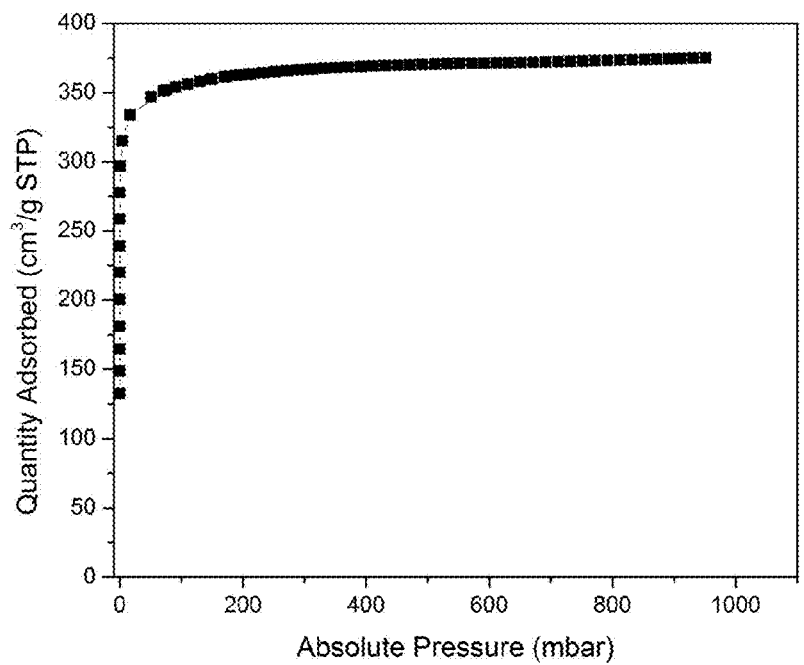
FIG. 6 shows the $N_2$ uptake (adsorption) measured for PCN-250 (Al).

FIG. 6 shows the N$_2$ uptake (adsorption) measured for PCN-250 (Al).

Figure 7:
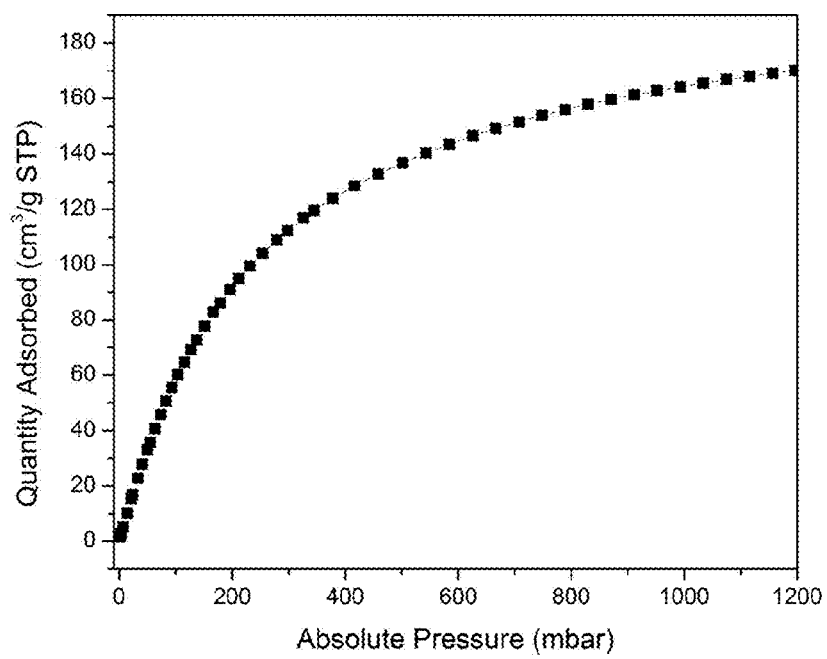
FIG. 7 shows the $CH_4$ uptake (adsorption) measured for PCN-250 (Al).

FIG. 7 shows the CH$_4$ uptake (adsorption) measured for PCN-250 (Al).

Figure 8:
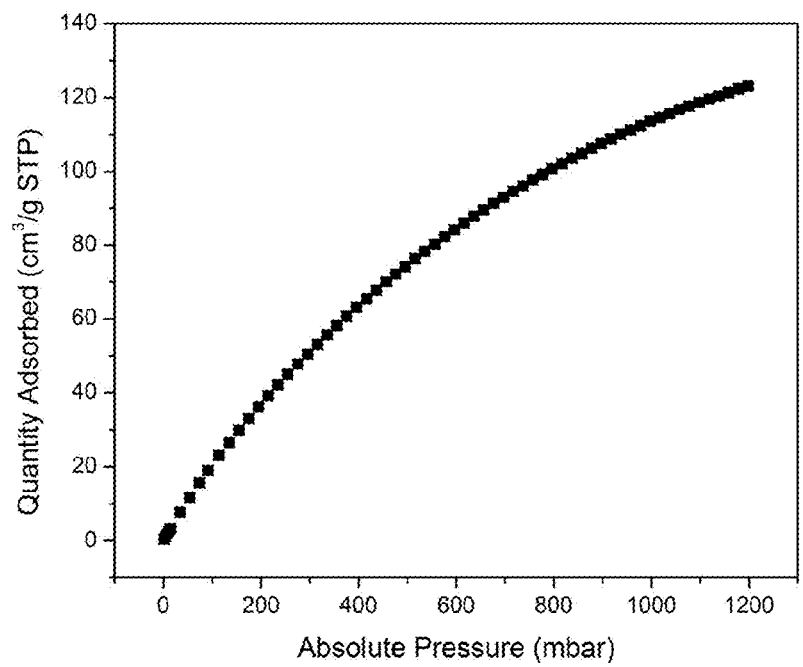
FIG. 8 shows the $CO_2$ uptake (adsorption) measured for PCN-250 (Al).

FIG. 8 shows the CO$_2$ uptake (adsorption) measured for PCN-250 (Al).

The uptake properties exhibited by PCN-250 (al) are observed to be excellent.

Thermogravimetric Analysis of PCN-250 (Al)

About 15 mg samples of PCN-250 (Al) was heated on a TGA-50 (Shimadzu) thermogravimetric analyzer from room temperature to 650° C. at a rate of 5° C. min$^{-1}$ under N$_2$ flow of 15 mL min$^{-1}$.

Figure 9:
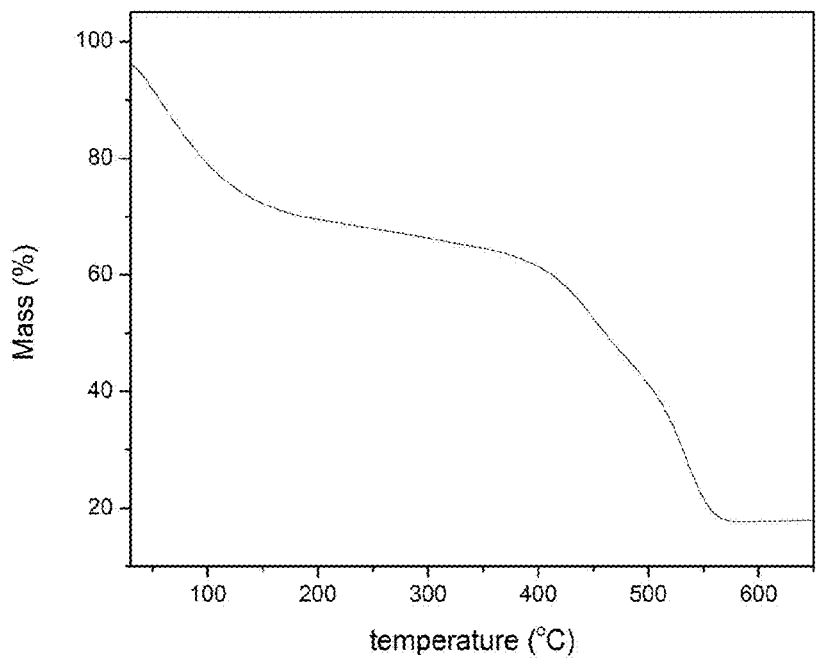
FIG. 9 shows a thermogravimetric analysis trace for a fresh sample of PCN-250 (Al).
Figure 10A:
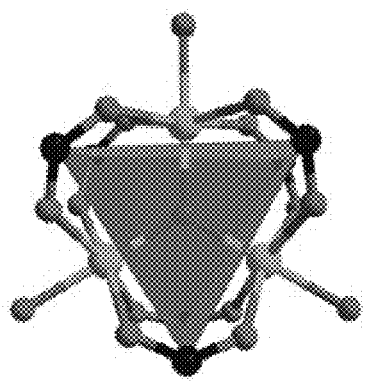
FIGS. 10a, b, & c show the crystallographic structure of the material obtained (PCN-250) represented schematically.
Figure 10B:
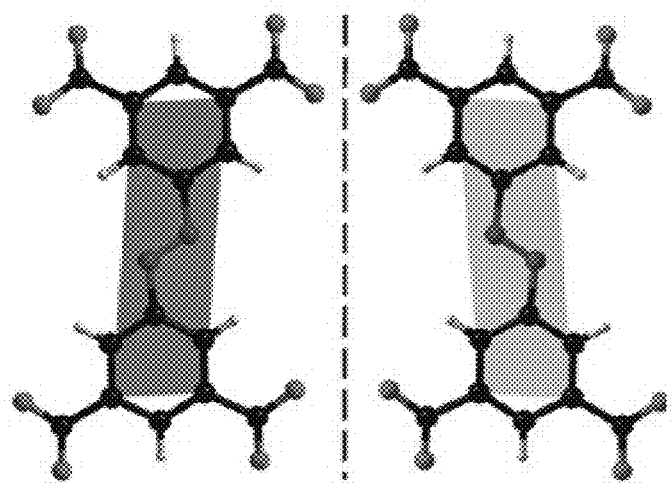
Figure 10C:
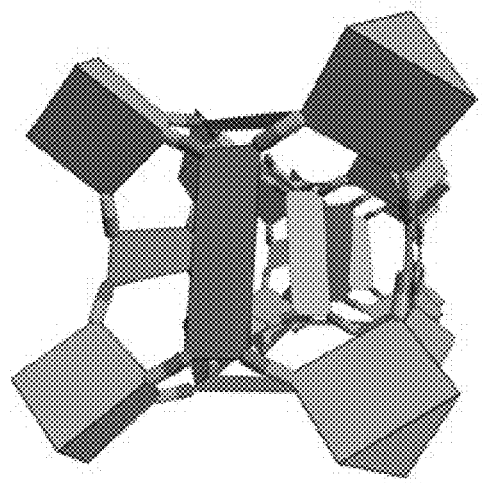

FIG. 9 shows the thermogravimetric analysis trace for a fresh sample of PCN-250 (Al).

The invention claimed is:

1. A single crystal metal-organic framework comprising one or more metal-ligand clusters, each metal-ligand cluster comprising (i) a metal cluster having an Al$_3$O cornerstone, and (ii) one or more ligands having two or more carboxylate groups;

wherein the single crystal has a size greater than or equal to 10 μm; the metal-organic framework comprises cavities having a free diameter of about 4 Å to about 40 Å; and the metal-organic framework comprising pores having a pore volume from about 0.1 cm$^3$/g to about 4 cm$^3$/g.

2. The single crystal metal-organic framework according to claim 1, wherein the crystal is monocrystalline.

3. The single crystal metal-organic framework according to claim 1, having a BET specific surface area of at least 200 m$^2$/g, at least 300 m$^2$/g, at least 600 m$^2$/g, or at least 800 m$^2$/g.

4. The single crystal metal-organic framework according to claim 1, having a surface area of less than or equal to 8000 m$^2$/g, less than or equal to 6000 m$^2$/g, or less than or equal to 4000 m$^2$/g.

5. The single crystal metal-organic framework according to claim 1, the metal-organic framework comprising cavities having a free diameter of from about 5 Å to about 25 Å, or from about 5 Å to about 15 Å.

6. The single crystal metal-organic framework according to claim 1, the metal-organic framework comprising pores having a pore volume from about 0.2 cm$^3$/g to about 3 cm$^3$/g.

7. The single crystal metal-organic framework according to claim 1, having a size greater than or equal to 20 μm, 30 μm, or 50 μm.

8. The single crystal metal-organic framework according to claim 1, having a crystal size from about 10 μm to about 2000 μm, or from about 50 μm to about 200 μm.

9. The single crystal metal-organic framework according to claim 1, wherein the one or more ligands are derived from a dicarboxylic acid, a tricarboxylic acid, a tetracarboxylic acid, a hexacarboxylic acid, or a octacarboxylic acid.

10. The single crystal metal-organic framework according to claim 1, wherein each metal cluster is coordinated with 4, 5, or 6 ligands.

11. The single crystal metal-organic framework according to claim 1, the metal-organic framework comprising inorganic cornerstones having at least 8 coordination sites, or at least 10 coordination sites, or having 12 coordination sites.

12. The single crystal metal-organic framework according to claim 1, having a molar ratio of metal ions to organic linker of from about 1:0.2 to about 1:0.7, or from about 1:0.45 to about 1:0.55.

13. A process of preparing a single crystal of a metal-organic framework as defined in claim 1, the process comprising reacting a starting compound of formula $Al_3O(CH_3COO)_6$ with a ligand precursor having at least two carboxylic acid groups in the presence of acetic acid to provide a metal-organic framework comprising a $Al_3O$ cluster where at least one ($CH_3COO$) ligand is replaced by at least one ligand having at least two carboxylate groups.

14. The process according to claim 13, wherein the process is a solvothermal process.

15. The process according to claim 14, wherein the process involves heating the reaction under pressure.

16. A method comprising uptaking at least one substance by a metal-organic framework according to claim 1; wherein the substance is hydrogen, methane, carbon dioxide or nitrogen.

17. A method of storing a gas in a metal-organic framework according to claim 1.

18. A method of adsorbing a guest molecule comprising contacting a metal-organic framework according to claim 1 with a guest molecule source; wherein the guest molecule is hydrogen, methane, carbon dioxide or nitrogen.

* * * * *